United States Patent [19]
Hyldig-Nielsen et al.

[11] Patent Number: 5,888,733
[45] Date of Patent: Mar. 30, 1999

[54] IN SITU HYBRIDIZATION TO DETECT SPECIFIC NUCLEIC ACID SEQUENCES IN EUCARYOTIC SAMPLES

[75] Inventors: Jens J. Hyldig-Nielsen, Holliston, Mass.; Karl-Johan Pluzek, Smorum; Tom Just, Copenhagen, both of Denmark

[73] Assignee: Dako A/S, Glostrup, Denmark

[21] Appl. No.: 724,824

[22] Filed: Oct. 2, 1996

Related U.S. Application Data

[60] Provisional application No. 60/007,659, Nov. 28, 1995, and provsional application No. 60/015,664, Apr. 19, 1996.

[30] Foreign Application Priority Data

Nov. 16, 1995 [DK] Denmark ................................. 1282/95
Apr. 16, 1996 [DK] Denmark ................................. 0445/96
Sep. 24, 1996 [WO] WIPO ..................... PCT/DK96/00406

[51] Int. Cl.⁶ .............................. C12Q 1/68; C07H 21/04; C07K 5/00
[52] U.S. Cl. ................................ 435/6; 536/243; 530/300
[58] Field of Search ................................. 435/6, 5, 810; 530/333, 334, 300; 536/18.7, 24.3

[56] References Cited

U.S. PATENT DOCUMENTS

| 5,173,401 | 12/1992 | Wolffe et al. | 435/6 |
| 5,217,866 | 6/1993 | Summerton et al. | 435/6 |
| 5,316,784 | 5/1994 | Maurer et al. | 427/2 |
| 5,378,606 | 1/1995 | Stern et al. | 435/6 |

FOREIGN PATENT DOCUMENTS

| 272009 | 6/1988 | European Pat. Off. | C12Q 1/68 |
| 131052 | 12/1993 | European Pat. Off. | C12Q 1/68 |
| WO 90/10715 | 9/1990 | WIPO | C12Q 1/68 |
| 9015159 | 12/1990 | WIPO | C07K 5/00 |
| 9220702 | 11/1992 | WIPO | C12K 1/68 |
| 9220703 | 11/1992 | WIPO | C12Q 1/68 |
| WO 92/22647 | 12/1992 | WIPO | C12N 15/00 |
| 9301498 | 1/1993 | WIPO | G01N 33/543 |
| WO 93/24652 | 12/1993 | WIPO | C12Q 1/68 |
| WO 94/02642 | 2/1994 | WIPO | C12Q 1/68 |
| WO 94/02645 | 2/1994 | WIPO | C12Q 1/68 |
| WO 95/08556 | 3/1995 | WIPO | C07H 21/00 |
| 9517430 | 6/1995 | WIPO | C07K 16/44 |
| WO 96/36734 | 11/1996 | WIPO | C12Q 1/68 |
| WO97/14026 | 4/1997 | WIPO . | |

OTHER PUBLICATIONS

Pluskal et al. Faseb Journal, Am. Soc. Biochem. Mol. Biol., vol. 8 Abstracts, Apr. 19, 1994.
Poster Presentation at 85th Annual Meeting Am. Soc. Biochem. Mol. Bio., May 21–25, 1994.
Nielson et al, Science, vol. 254, 1497–1500 (1991).
Hyrup et al, J. Am. Chem. Soc., vol. 116, 7964–7970 (1994).
Hanvey et al, Science, vol. 258, 1481–1485 (1992).
Rose, Anal. Chem.,vol. 65 3545–3549 (1993).
Egholm et. al; Nature, 365; 566–568 (1993).
Nielsen et al, BioConj. Chem., 5; 3–7 (1994).
Egholm et al, J.A.C.S. 114; 1895–1897 (1992).
Young et al, Nucleic Acid Hybridization, JDL Press (1985) pp. 62–65.
Johannsson et al; ELISA and Other Solid Phase Immunology, John Wiley & Sons (1988) pp. 85–106.

*Primary Examiner*—W. Gary Jones
*Assistant Examiner*—Debra Shoemaker
*Attorney, Agent, or Firm*—Graham & James LLP

[57] ABSTRACT

Methodologies for determining the presence of specific nucleic acid sequences in a sample of eucaryotic origin using in situ hybridization are described. The in situ hybridization is performed using a hybridization solution comprising at least one binding partner capable of hybridizing to the specific nucleic acid sequence to be determined so as to form hybrids and a hybrid destabilizing agent in an amount effective to decrease the melting temperature of hybrids formed between the nucleic acid and the binding partner so as to increase the specific binding and decrease the non-specific binding. The binding partner used is a polymeric strand of polymerized moieties having a non-cyclic backbone, the polymeric strand being capable of hybridizing to the nucleic acid sequence to be determined. The method is particularly suitable for diagnosing different human diseases such as bacterial and viral infections, genetic diseases and neoplastic disorders.

23 Claims, No Drawings

IN SITU HYBRIDIZATION TO DETECT SPECIFIC NUCLEIC ACID SEQUENCES IN EUCARYOTIC SAMPLES

The present application claims priority under 35 USC 119(e)(1) from Provisional Application Nos. 60/007,659, filed Nov. 28, 1995 and 60/015,664 filed Apr. 19, 1996.

The present invention relates to methods for determining the presence of specific nucleic acid sequences in a sample of eucaryotic origin using in situ hybridization. The present method is particularly suitable for diagnosing different diseases such as bacterial and viral infections, genetic diseases and neoplastic disorders. In another aspect of the present invention, diagnostic kits are provided for use in performing the method according to the invention.

BACKGROUND OF THE INVENTION

Hybridization has traditionally been used to describe the general technique by which complementary strands of deoxyribonucleic acid (DNA) molecules, ribonucleic acid (RNA) molecules or combinations of DNA and RNA are separated into single strands and then allowed to renature or reanneal and reform base-paired double helices. Hybridization techniques are generally classified in three major classes: solution hybridization whereby the individual cell is disrupted and the internal nucleic acid is extracted into solution prior to hybridization; this technique includes different levels of purification of the nucleic acid prior to hybridization; filter or blot hybridization, whereby DNA or RNA is bound to a solid matrix either directly or after separation of the individual nucleic acid fragments on e.g. an agarose gel or a polyacrylamide gel and the subsequent hybridization is carried out with a labelled probe for detection of hybrids; and in situ hybridization (ISH) whereby a method is provided for the detection and localization of specific nucleic acid sequences directly in a specific structure, e.g. within a cell, a tissue, a nucleus or a chromosome. Although these techniques are based on the specific interaction between the target and a probe capable of binding specifically to the sequence to be detected, these techniques are quite different and distinguishable from each other.

In situ hybridization allows detection of specific cellular or chromosomal nucleic acid sequences in the cellular material such as in paraffin-embedded tissue sections, fresh or frozen biopsies, cells or chromosomes. Traditionally, nucleic acid probes having a base sequence that is sufficient complementary to the target sequence to be detected have been used. For this type of detection, nucleic acid probes labelled with detectable groups other than radioisotopes have been used widely.

The demand for more sensitive methods is increasing. Ways of increasing the sensitivity are to use an enhancing detection system and/or to increase the number of probes with different sequences targeting the nucleic acid sequences to be detected. When closely related sequences are to be distinguished, it is often limited how many probe variations can be used to detect a given target.

An increase of the sensitivity for in situ nucleic acid hybridization in tissue sections or cell smears has been described using the so-called "in situ PCR". The principle of in situ PCR is to combine the techniques of PCR and ISH through the amplification of specific nucleic acid sequences inside the individual cells, resulting in an increase of copy numbers to levels detectable by ISH. Reproducible results depend on the integrity of the sample. During pretreatment of the sample, the cell membrane may be damaged giving rise to a risk of so-called "diffusion artefacts". PCR products may leak out of cells and serve as template for extracellular amplification. This may give rise to false positive signals. A recent report summerizes the pitfalls of "in situ PCR" (Cell Vision, 3, 231–235 (1995)).

In accordance with the present invention binding partners and protocols are provided for in situ hybridization procedures for the detection of specific nucleic acid sequences in a sample of eucaryotic origin. In the present method, hybridization is performed using a binding partner, which is a polymeric strand of polymerized moieties having a non-cyclic backbone, the polymeric strand being capable of hybridizing to the nucleic acid sequence to be determined. Examples of such polymeric strands are given in WO 92/20702.

In WO 92/20702, the term Peptide Nucleic Acid (PNA) was introduced to describe some compounds having a non-cyclic backbone and nucleic acid binding properties.

In WO 93/24652, PNA probes have been postulated to be feasible for in situ hybridization carried out without addition of a denaturing agent, such as formamide, and further with hybridization performed at low temperature. The postulated simplification of the in situ hybridization procedure is based on the prior assumption that PNA form triplex structures with double-stranded DNA. In WO 93/24652, there is no experimental data to support this simplification. It has now been shown that the hypothesis of triplex formation put forward in 1991 (Science, 254, 1497–1500 (1991)) only applies if a homopyrimidine PNA is combined with a homopurine DNA whereby $(PNA)_2$/DNA triplexes are formed, such as $(PNA(T))_2(polydA)$ (TIBTECH, 11, 384–386 (1993)).

SUMMARY OF THE INVENTION

In accordance with the present invention, methods are provided for determining the presence of specific nucleic acid sequences in samples of eucaryctic origin using in situ hybridization.

The present invention thus provides a method for determining the presence of specific nucleic acid sequences in a sample of eucaryotic origin using in situ hybridization comprising the steps of (1) producing a preparation of said sample, whereby the sample will be subject to a fixation, (2) contacting said preparation with a hybridization solution comprising at least one binding partner capable of hybridizing to a specific nucleic acid sequence to be determined so as to form hybrids and a hybrid destabilizing agent in an amount effective to decrease the melting temperature of hybrids formed between said nucleic acid and said binding partner so as to increase the ratio between specific binding and non-specific binding, said binding partner being a polymeric strand containing polymerized moieties having a non-cyclic backbone, the polymeric strand being capable of hybridizing to the nucleic acid sequence to be determined, (3) removing any unbound and any non-specifically bound binding partner, and (4) determining the presence of bound binding partner in the preparation.

In an embodiment of the present invention, a method is provided, wherein the polymeric strand comprises polymerized moieties of formula (I)

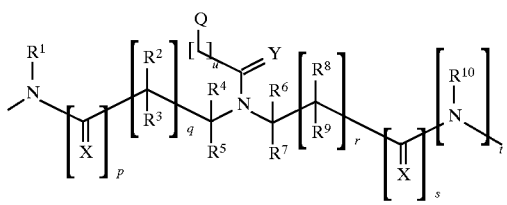

wherein Y designates O or S, each X independently designates O or S, each Q designates a ligand that independently is a naturally occurring nucleobase, a non-naturally occurring nucleobase, an intercalator, a nucleobase-binding group, a label or H, u is an integer of from 1 to 5, p and s independently designate 0 or 1, q and r independently designate 0 or 1, t designates 0 or 1, $R^1$ and $R^{10}$ independently designate H or $C_{1-4}$ alkyl, $R^2, R^3, R^4, R^5, R^6, R^7, R^8$ and $R^9$ independently designate H, the side chain of a naturally occurring amino acid or the side chain of a non-naturally occurring amino acid.

The hybrid destabilizing agent is present in amount effective to decrease the melting temperature of hybrids formed between the nucleic acid to be determined and the binding partner used to detect said nucleic acid so as to increase the ratio between specific binding and non-specific binding.

Examples of hybrid destabilizing agents are formamide, ethylene glycol and glycerol. These agents may preferably be present in an amount of above 10% and less than 70%. Formamide may more preferably be present in an amount of from 20% to 60%, most preferably of from 30% to 50%. Ethylene glycol may more preferably be present in an amount of from 30% to 65%, most preferably of from 50% to 65%.

The present invention provides a method for determining the presence of specific nucleic acid sequences in samples of eucaryotic origin, such as of human, animal or plant origin. Non-limiting examples are tissue sections, cell smears, suspensions of cells or parts thereof and chromosome spreads.

The binding partner may suitably be labelled or unlabelled. In one aspect, the binding partner carries one or more labels for detection of hybrids formed during hybridization.

In one embodiment of the present invention, a washing buffer at alkaline pH may preferably be used in step (3). The use of a washing buffer having an alkaline pH may in some cases provide an increased ratio between specific binding and non-specific binding.

In a further aspect of the invention, a diagnostic kit for use in performing the method according to the invention is provided, which kit comprises one or more binding partners as defined above.

The diagnostic kit may further include reagents required for sample preparation, a hybrid destabilizing agent and optionally reagents for the detection of the hybrids formed after hybridization.

SPECIFIC DESCRIPTION

The method for determining the presence of specific nucleic acid sequences in samples of eucaryotic origin using in situ hybridization comprises the following four steps: (1) producing a preparation of the sample, (2) hybridization, (3) post-hybridization washing to remove any unbound and any non-specifically bound binding partner, and (4) determination of the presence of bound specific binding partner in the preparation. Embodiments of these steps are described below together with examples of starting material and the binding partners to be used in the hybridization.

Starting material

The present method can be used to detect nucleic acid sequences in samples of eucaryotic origin. It is contemplated that the present method provides a valuable tool for analysing such samples for the presence of nucleic acid sequences specific for e.g. pathogenic bacteria or virus hence providing information for establishing a diagnosis. In human or animal pathology, the detection of chromosomal aberrations may provide clinically important information for diagnosing genetic disorders or diseases. In plant biology, it is further contemplated that the present method may be a valuable tool for monitoring the efficiency of transferring for example herbicide resistance genes to a plant or, like in human tissues, to establish specific synthesis of proteins (by detection of mRNA) in a given cell structure.

The term "sample of eucaryotic origin" includes, but is not limited to samples of human, animal or plant origin. In the present context, the term "sample" is intended to include, but is not limited to, human, animal or plant tissue sections, cell or tissue cultures, suspension of human, animal or plant cells or isolated parts thereof, human or animal biopsies, blood samples, saliva, urine, cerebrospinal fluid, milk, excretions, secretions, swabs, faecal samples and aspirates.

It is envisaged that in the hybrids formed between the present binding partners and the specific nucleic acids to be determined Hoogsteen and/or Watson-Crick base pairing assist in the formation of the hybrids. In the present context, the term "hybrids" is intended to include complexes of the present binding partners and the specific nucleic acid to be determined comprising two or more strands. Non-limiting examples are duplexes of a single strand of the present binding partner and a single strand of the nucleic acid and triplexes of e.g. two strands of the present binding partner and one strand of the nucleic acid.

Producing a preparation of the sample

The sample to be examined is pre-treated before the hybridization step whereby a preparation of the sample is produced. The person skilled in the art will readily recognize that the appropriate pretreatment will depend on the type of sample to be examined. During the pretreatment, the sample will be subject to a fixation.

Thus, in one embodiment of the method, the sample is deposited onto a solid support. Techniques for depositing a sample onto the solid support will depend upon the type of sample in question and may include, for example, sectioning of tissue as well as smearing or cytocentrifugation of cell suspensions. Many types of solid supports may be utilized to practice the present method. The use of such supports and the procedures for depositing samples thereon are known to those skilled in the art. Glass microscope slides are especially convenient. Glass microscope slides can be treated to better retain the sample.

Prior to hybridization, the sample is suitably pre-treated with various chemicals to facilitate the subsequent reactions. The actual pretreatment will depend on the type of sample to be analysed and on whether DNA or RNA sequences are to be detected. For localizing RNA such as mRNA, it is advantageous that the sample is treated as soon as possible after sample collection to retain most of the RNA intact. If DNA sequences are to be detected, this step is less important. The preferred treatment is one which fixes and preserves the morphological integrity of the cellular matrix and of the nucleic acids within the cell as well as enables the most efficient degree of probe penetration. The terms "probe" and "binding partner" are used interchangeably herein and thus the term "binding partner" corresponds to the term "probe" which is traditionally used in nucleic acid hybridization.

In producing a preparation of a tissue sample, the morphological integrity of a tissue and the integrity of the nucleic acids can be preserved by bringing the sample to a fixed stage either by means of chemical fixation or freezing. When freezing is used for preservation of for instance a biopsy, the biopsy is typically frozen in liquid nitrogen. After freezing, the sample may appropriately be stored at −80° C. Prior to the analysis of the nucleic acid, the frozen sample is cut into thin sections and transferred to e.g. pre-treated slides. This can e.g. be carried out at a temperature of −20° C. in a cryostat. The biopsy or tissue sections may suitably be stored at −80° C. until use. Prior to hybridization, the tissue section may be treated with a fixative, preferably a precipitating fixative such as acetone or the tissue section is incubated for a short period in a solution of buffered formaldehyde. Alternatively, the biopsy or tissue section can be transferred to a fixative such as buffered formaldehyde for 12 to 24 hours. Following fixation, the tissue may be embedded in paraffin forming a block from which thin sections can be cut. Well prepared paraffin-embedded samples can be stored at room temperature for a period of years.

Prior to hybridization, the tissue section is dewaxed and rehydrated using standard procedures.

Further permeabilization may be necessary in order to ensure sufficient accessibility of the target nucleic acid sequences to the binding partner. The type of treatment will depend on several factors, for instance on the fixative used, the extent of fixation, the type and size of sample used and the length of the binding partner. The treatment may involve exposure to protease such as proteinase K, pronase or pepsin, diluted acids, detergents or alcohols or a heat treatment.

In some cases, a prehybridization step using a prehybridization mixture very similar to the hybridization solution but without the binding partner, might be useful in order to decrease non-specific binding of the binding partner. The components of the prehybridization mixture should be selected so as to obtain an effective saturation of sites in the tissue that might otherwise bind the binding partner non-specifically.

For analysing a suspended preparation such as a suspension of cells, the sample is treated so as to obtain a permeabilization of the material and a preservation of the morphology. Fixation may be carried out with a fixative such as formaldehyde, acetone or ethanol.

In another aspect, the present method permits the detection of a specific nucleic acid sequence in a chromosome. Such detection may for example be carried out using spreads of chromosomes in metaphase, where the target sequence may be located in any region of the chromosomes, e.g. the centromeric region or the telomeric region of a chromosome. A pretreatment may in this case comprise adding an agent such as colcemide to arrest the chromosomes of dividing cells in the metaphase of the mitosis. Subsequently, the sample may be treated with a hypotonic buffer. Following centrifugation, the chromosomes are treated with a fixative and spread on a slide. Immediately before or simultaneously with the hybridization step, the preparation may be treated to separate the double-stranded target. This separation can be achieved by heating the preparation in the presence of a denaturing agent such as formamide. The detection of a specific nucleic acid sequence in a chromosome may also be carried out using chromosomes in interphase, e.g. in tissue sections or in a suspension of cells. In such cases, the specimens may be treated as described above for tissue sections or suspension of cells.

For all sample preparations, the nucleic acids are fixed in a morphological structure allowing hybridization to be carried out in situ. Thus, the nucleic acids are not extracted from the cellular material and the hybridization is not carried out in solution.

If RNA sequences are the target for detection, it is important to avoid degradation of the target nucleic acids by ribonucleases during the prehybridization steps. It is thus important that all equipment and solutions used for pretreatment as well as for hybridization are appropriately treated to remove nucleases. Such inactivation techniques are well known in the literature and may be performed according to standard procedures.

Binding partner to be used in the present method

The binding partner used in the present method is a polymeric strand of polymerized moieties having a non-cyclic backbone, the polymeric strand being capable of hybridizing to the nucleic acid sequence to be determined.

In one embodiment of the method, the polymeric strand comprises polymerized moieties of formula (I)

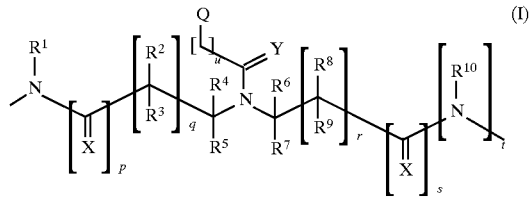

wherein Y designates O or S, each X independently designates O or S, each Q designates a ligand that independently is a naturally occurring nucleobase, a non-naturally occurring nucleobase, an intercalator, a nucleobase-binding group, a label or H, u is an integer from 1 to 5, p and s independently designate 0 or 1, q and r independently designate 0 or 1, t designates 0 or 1, $R^1$ and $R^{10}$ independently designate H or $C_{1-4}$ alkyl, $R^2, R^3, R^4, R^5, R^6, R^7, R^8$ and $R^9$ independently designate H, the side chain of a naturally occurring amino acid or the side chain of a non-naturally occurring amino acid.

The term "naturally occurring nucleobases" includes the four main DNA bases (i.e. thymine (T), cytosine (C), adenine (A) and guanine (G)) as well as other naturally occurring nucleobases (e.g. uracil (U) and hypoxanthine).

The term "non-naturally occurring nucleobases" comprises, e.g., naturally occurring nucleobases wherein a label is coupled to the base optionally through a suitable linker, and modified naturally occurring nucleobases such as, e.g., modified uracil and hypoxanthine. Other examples of non-naturally occurring nucleobases are 2,6-diaamino purine, propynylcytosine (C propynyl), isocytosine (iso-C), isoguanosine 5-methyl-isocytosine (iso$^{Me}$C) (see e.g. Tetrahedron Letters Vol 36, No 12, 2033–2036 (1995) or Tetrahedron Letters Vol 36, No 21, 3601–3604 (1995)).

Examples of useful intercalators are e.g. acridin, antraquinone, psoralen and pyrene.

Examples of useful nucleobase-binding groups are e.g. 3-nitro pyrrole and 5-nitro indole.

In the present context, "$C_{1-4}$ alkyl" is intended to mean branched or non-branched alkyl groups containing 1 to 4 carbon atoms. Non-limiting examples are $CH_3$, $CH_2CH_3$ and $CH(CH_3)_2$.

Within the present context, the expression "naturally occurring amino acid" is intended to comprise D- and L-forms of amino acids commonly found in nature, e.g. D- and L-forms of Ala (alanine), Arg (arginine), Asn (aspargine), Asp (aspartic acid), Cys (cysteine), Gln (glutamine), Glu (glutamic acid), His (histidine), Ile (isoleucine), Leu (leucine), Lys (lysine), Met (methionine), Phe (phenylalanine), Pro (proline), Ser (serine), Thr (threonine), Trp (tryptophan), Tyr (tyrosine) and Val (valine).

In the present context, the expression "non-naturally occurring amino acid" is intended to comprise D- and L-forms of amino acids other than those commonly found in nature as well as modified naturally occurring amino acids. Examples of useful non-naturally occurring amino acids are D- and L-forms of Cha (cyclohexylalanine), Cit (citrulline), Hci (homocitrulline), HomoCys (homocystein), Hse (homoserine), Nle (norleucine), Nva (norvaline), Orn (ornithine), Sar (sarcosine) and Thi (thienylalanine).

The binding partner to be used in the present method should comprise a sufficient number of ligands capable of interacting with the nucleotide sequence to be determined to form hybrids sufficiently stable under the stringency used in the hybridization and in the post-hybridization wash (steps (2) and (3)). The strategy for selecting the ligands of the binding partner to be used in accordance with the present method may be based on available target nucleotide sequence information.

In the above-indicated binding partners, the backbone of the moieties may preferably consist of six atoms. This has been shown to provide the presently strongest observed affinity for nucleic acids. It may in some cases be advantageous to change the strength of the binding between the binding partner and the nucleic acid sequence. Such change of the affinity may be accomplished by separating the ligands by fewer or by more atoms than six atoms. It is contemplated that preferred binding partners to be used in the present method comprise less than 25% by weight (calculated excluding X and Q groups as well as any linkers and/or labels) of moieties having more or less than six atoms in the backbone.

The strength of the binding between the binding partner and the nucleic acid sequence is influenced by the ligand Q. Hoogsteen and/or Watson-Crick base pairing assist in the formation of hybrids between a nucleic acid and a binding partner wherein Q designates a nucleobase. It is contemplated that one or more of the ligands may be a group which contribute little or none to the binding of the nucleic acid such as hydrogen. It is contemplated that binding partners to be used in the present method comprise less than 25% by weight moieties wherein Q designate H. One or more of the ligands Q may be groups that stabilize nucleobase stacking such as intercalators.

In the above-indicated binding partners, one or more of the Q-groups may designate a label. Examples of suitable labels are given below. Moieties wherein Q denotes a label may preferably be located in one or both of the terminating moieties of the polymeric strand. Moieties wherein Q denotes a label may also be located internally.

Suitable binding partners to be used in the present method are binding partners comprising polymerized moieties of formula (I) wherein u, p, q, r, s, Y, X and Q are as defined above, t is 0, $R^1$ designates H or $CH_3$, $R^3$, $R^4$, $R^6$ and $R^9$ designate H, and $R^2$, $R^5$, $R^7$ and $R^8$ independently designate H or the side chain of a naturally occurring amino acid or the side chain of a non-naturally occurring amino acid.

Another embodiment relates to a method, wherein the polymeric strand comprises polymerized moieties of formula (II), which are moieties of the general formula (I) wherein r is 0 and q and s are 1,

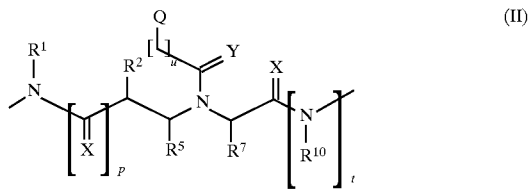

(II)

wherein Y, X, Q, p, t and u are as defined above, $R^2$, $R^5$ and $R^7$ independently designate H, the side chain of a naturally occurring amino acid or the side chain of a non-naturally occurring amino acid, and $R^1$ and $R^{10}$ independently designate H or $CH_3$.

Yet another embodiment relates to a method, wherein the polymeric strand comprises polymerized moieties of formula (III), which are moieties of the general formula (I) wherein p, r and t are 0 and q and s are 1

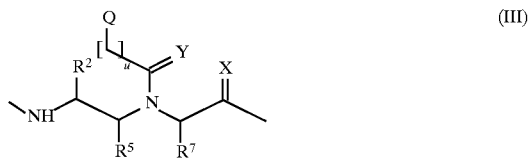

(III)

wherein Y, X, Q and u are as defined above, $R^2$, $R^5$ and $R^7$ independently designate H, the side chain of a naturally occurring amino acid or the side chain of a non-naturally occurring amino acid.

The polymeric strand comprises polymerized moieties as defined above. From the formula, it is to be understood that the polymeric strand may comprise polymerized moieties which structure may be mutually different or identical.

The backbone of the polymeric strand may suitably form a polyamide comprising polymerized moieties, wherein all X groups are O, or form a polythioamide comprising polymerized moieties, wherein all X groups are S. The polyamide and polythioamide forming moieties may be linked to form polymeric strands comprising both polyamide and polythioamide forming moieties or to form polymeric strands comprising polyamide forming moieties or polythioamide forming moieties only. Polymeric strands having a polyamide backbone (all X groups designate O) are of particular interest.

Binding partners of great interest are those wherein the polymeric strand comprises polymerized moieties of formulas (IV)–(VI), which are moieties of the general formula (I) wherein p, r and t are 0 and u, s and q are 1:

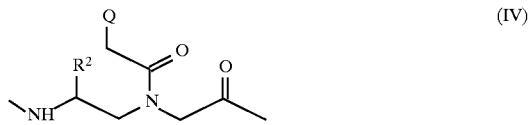

(IV)

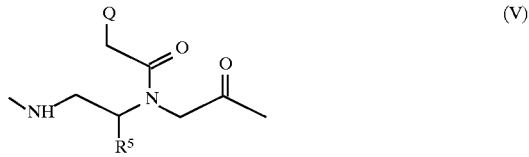

(V)

-continued

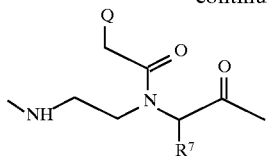
(VI)

wherein $R^2$, $R^5$ and $R^7$ independently designate H, the side chain of a naturally occurring amino acid or the side chain of a non-naturally occurring amino acid, and each Q independently designates a naturally occurring nucleobase, a non-naturally occurring nucleobase, an intercalator or a nucleobase-binding group.

In formulas (IV)–(VI), the substituents $R^2$, $R^5$ and $R^7$ may suitable be chosen so as to designate H or the side chain of Ala, Asp, Cys, Glu, His, HomoCys, Lys, Orn, Ser or Thr, and Q to designate thymine, adenine, cytosine, guanine, uracil or hypoxanthine.

Particularly interesting binding partners are those wherein the polymeric strand comprises polymerized moieties of formula (VII) which are moieties of the general formula (I) wherein p, r and t are 0 and u, s and q are 1,

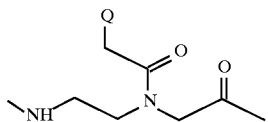
(VII)

wherein Q designates thymine, adenine, cytosine, guanine, uracil or hypoxanthine.

The preferred length of the binding partner will depend on the target material and whether labelled binding partners are used. It is contemplated that especially interesting binding partners comprise from 8 to 30 polymerized moieties as defined above. Binding partners comprising from 12 to 20 polymerized moieties may be of particular interest, and binding partners comprising from 14 to 20 moieties are of most interest.

As mentioned above, the polymerized moieties of the binding partner may be mutually different or identical. In some embodiments, the polymerized moieties of formulas (IV)–(VII) constitute at least 75% by weight (calculated as defined above), preferably at least 80% by weight and most preferably at least 90% by weight of the polymeric strand.

The ends on the moieties terminating the polymeric strand may be substituted by suitable substituents. The substituents may be chosen so as to form the free or acylated form of the terminating moiety. The substituents may further be chosen so as to form an ester, an amide or an amine depending on the chemical nature of the terminating moiety. A terminating end may further be substituted by one or more labels, which labels may be incorporated end to end, i.e. so as to form a non-branched labelled end, or may be incorporated so as to form a branched labelled end ("zipper"). A terminating end may further be substituted by one or more linker units. Such linker units may be attached directly to a terminating end, may be attached to a label or between labels on a terminating end, or be attached to a terminating end before a label is attached to a terminating end. It should be understood that two terminating ends may carry different or identical substituents, linker units and/or labels. It should further be understood that the term "a label" is intended to comprise one or more labels.

The expression "peptide label" is intended to mean a label comprising from 1 to 20 naturally occurring or non-naturally occurring amino acids, preferably from 1 to 10 naturally occurring or non-naturally occurring amino acids, more preferably from 1 to 8 naturally occurring or non-naturally occurring amino acids, most preferably from 1 to 4 naturally occurring or non-naturally occurring amino acids, linked together end to end in a non-branched or branched ("zipper") fashion. In a preferred embodiment, such a non-branched or branched end comprises one or more, preferably from 1 to 8 labels, more preferably from 1 to 4, further labels other than a peptide label. Such further labels may suitably terminate a non-branched end or a branched end. One or more linker units may suitably be attached to the terminating end before a peptide label and/or a further label is attached. Such linker units may also be attached between a peptide label and a further label.

The polymeric strand as such may also comprise one or more labels such as from 1 to 8 labels, preferably from 1 to 4 labels, and/or one or more linker units, which may be attached internally, i.e. to the backbone of the polymeric strand. The linker units and labels may mutually be attached as described above.

In the present context, the term "label" refers to a substituent which is useful for detection of hybrids formed between a binding partner and a nucleic acid. In accordance with the present invention, suitable labels comprise fluorophores, biotin, dinitro benzoic acid, digoxigenin, radioisotope labels, peptide or enzyme labels, chemiluminescence labels, hapten, antigen or antibody labels. Examples of particular interesting labels are biotin, fluorescent labels, such as fluorescein labels, e.g. 5-(and 6)-carboxyfluorescein, 5- or 6-carboxyfluorescein, 6-(fluorescein)-5-(and 6)-carboxamido hexanoic acid and fluorescein isothiocyanate, peptide labels, dinitro benzoic acid, rhodamine, tetramethylrhodamine, cyanine dyes such as Cy2, Cy3 and Cy5, coumarin, R-phycoerythrin, allophycoerythrin, Texas Red and Princeton Red as well as conjugates of R-phycoerythrin and, e.g. Cy5 or Texas Red.

Examples of preferred labels are biotin, fluorescent labels, peptide labels and dinitro benzoic acid. Peptide labels may preferably be composed of from 1 to 10, more preferably of from 1 to 8, most preferably of from 1 to 4, naturally occurring or non-naturally occurring amino acids. It may be particularly advantageous to incorporate one or more other labels as well as a peptide label such as from 1 to 8 or from 1 to 4 other labels. Two of such other labels may e.g. be incorporated at each terminating end.

Suitable peptide labels may preferably be composed of cysteine, glycine, lysine or ornithine.

A linker may be made up of linker units selected from units of formulas —NH—$(CH_2CH_2O)_nCH_2C(O)$—, —NH $(CHOH)_nC(O)$—, —$(O)C(CH_2OCH_2)_nC(O)$— and —NH $(CH_2)_nC(O)$—, wherein n is 0 or an integer from 1 to 8, preferably from 1 to 3. A linker unit may have a free amino group or a free acid group, i.e. $NH_2(CH_2CH_2O)_nCH_2C(O)$—, $NH_2(CHOH)_nC(O)$—, $HO(O)C(CH_2OCH_2)_nC(O)$—, $NH_2(CH_2)_nC(O)$—, —$NH(CH_2CH_2O)_nCH_2C(O)OH$, —$NH(CHOH)_nC(O)OH$, —$(O)C(CH_2OCH_2)_nC(O)OH$ and —$NH(CH_2)_nC(O)OH$. A linker may consist of up to 3 of such linker units. Examples of very interesting linker units are —$NHCH_2C(O)$—, —$NHCH_2CH_2C(O)$—, —NH $(CH_2CH_2O)_2CH_2C(O)$—, $HO(O)CCH_2C(O)(NH$— $(CH_2CH_2O)_2CH_2C(O))_2$—.

In a further embodiment, the ligand Q as defined above may be labelled. Suitable labels are as defined above. Between such a label, a linker selected from $C_{1-15}$ alkyl, $C_{1-5}$ alkenyl and $C_{1-5}$ alkynyl may be incorporated. In the present context, "$C_{1-15}$ alkyl, $C_{1-15}$ alkenyl and $C_{1-5}$ alkynyl" are intended to mean branched or non-branched alkyl, alkenyl and alkynyl groups containing from 1 to 15 carbon atoms. It is preferred that such labelled ligands Q are selected from thymine and uracil labelled in the 5 position.

In a preferred embodiment, the polymeric strands used are binding partners comprising polymerized N-(2-aminoethyl) glycine moieties of formula (VII) wherein the glycine nitrogen is connected to naturally occurring nucleobases by a methylene carbonyl linker. The binding partners to be used as detection probes may suitably comprise from 8 to 30 of such polymerized moieties, preferably comprise from 12 to 20 moieties, most preferably from 14 to 20 moieties.

Preparation of embodiments of binding partners for hybridization

In one embodiment, the presently most preferred binding partner is a polymeric strand comprising polymerized moieties of formula (VII). The synthesis of compounds of this structure are described in WO 92/20702, and these compounds have been named PNA.

The binding partners used in the examples were synthesized according to the procedures described in "PNA Information Package" obtained from Millipore Corporation (Bedford, Mass., U.S.A.) or the binding partners were obtained from PerSeptive Biosystems (Framingham, Mass., U.S.A.).

If using the Fmoc strategy for elongation of the binding partner with linkers or amino acids, it was possible to have side chain amino groups protected with acid sensitive protection groups such as the Boc group. This method allows introduction of a linker containing several Boc protected amino groups which can all be cleaved and labelled in the same synthesis cycle.

One way of labelling the binding partner is to use a fluorescent label, such as 5-(and 6)-carboxyfluorescein, 5- or 6-carboxyfluorescein, 6-(fluorescein)-5-(and 6)-carboxamido hexanoic acid or fluorescein isothiocyanate. The acid group is activated with HATU (O-(7-azabenzotriazol-1-yl)-1,1,3,3-tetramethyluronium hexafluorophosphate) or HBTU (2-(1H-benzotriazol-1-yl)-1,1,3,3-tetramethyluronium hexafluorophosphate) and reacted with the N-terminal amino group. The same technique can be applied to other labelling groups containing an acid function. Alternatively, the succinimidyl ester of the above-mentioned labels may be used directly.

After synthesis, the binding partners were cleaved from the resin using standard procedures as described by Millipore Corporation or PerSeptive Biosystems. The binding partners were purified and analysed using reversed-phase HPLC techniques at 50° C. and were characterized by matrix-assisted laser desorption/ionization time of flight mass spectrometry (MALDI-TOFMS), plasma desorption mass spectrometry (PDMS) or electron spray mass spectrometry (ESMS).

Generally, binding partners such as binding partners comprising polymerized moieties of formula (IV)–(VII) may also be prepared as described in, e.g., Tetrahedron Letters Vol 35, No 29, 5173–5176 (1994) and Bioorganic & Medical Chemistry Letters, Vol 4, No 8, 1077–1080 (1994). Chemical properties of some binding partners are described in, e.g., Nature, 365, 566–568 (1993).

Hybridization

The hybridization can be performed using fixed, immobilized or suspended preparations which are prepared as described above. If double-stranded target such as chromosomal or DNA sequences are to be detected, a treatment to separate the two strands may be necessary. This separation of the strands can be achieved by heating the sample in the presence of the hybridization mixture to a temperature sufficiently high and for a time period sufficiently long to dissociate the strands. Typically, heating at a temperature of 90° C. to 95° C. for a period of 5 to 15 minutes is suitable.

The hybridization buffer comprises a hybrid destabilizing agent in an amount effective to decrease the melting temperature of hybrids formed between the nucleic acid to be determined and the binding partner so as to increase the ratio between specific binding and non-specific binding. This agent will allow the hybridization to take place at a lower temperature than without the agent. In traditional nucleic acid hybridization, such agent is called a denaturing agent.

Hybridization and denaturing may be carried out simultaneously using a suitable amount a hybrid destabilizing agent in combination with a suitable temperature for the treatment.

The effective amount of the hybrid destabilizing agent will depend on the type of destabilizing agent used and furthermore on the binding partner or combination of binding partners used. It has been found that using binding partners of formula (VII), particular good results have been obtained by including a hybrid destabilizing agent. Examples of hybrid destabilizing agents are formamide, ethylene glycol and glycerol and these agents may preferably be used in a concentration above 10% and less than 70%. The concentration of formamide may more preferably be from 20% to 60%, most preferably from 30% to 50%. The concentration of ethylene glycol may more preferably be from 30% to 65%, most preferably centration of glo 65%. The concentration of glycerol may more preferably be from 45% to 60%, most preferably 50%.

It is often advantageous to include macromolecules or polymers such as dextran sulphate, polyvinylpyrrolidone and/or ficoll. In the presence of such macromolecules or polymers, the effective concentration of the binding partner at the target is assumed to be increased. Dextran sulphate may be added in a concentration of up to 15%. Concentrations of dextran sulphate of from 2.5% to 12.5% are often advantageous.

In some cases, it may be advantageous to add a detergent such as sodium dodecyl sulphate, Tween 20® or Triton X-100®.

During hybridization, other important parameters are hybridization temperature, concentration of the binding partner and hybridization time. The person skilled in the art will readily recognize that optimal conditions for various starting materials will have to be determined for each of the above-mentioned parameters.

The hybridization between binding partners comprising polymerized moieties of formulas (IV)–(VII) and a target nucleic acid sequence appears to be insensitive to variations in pH and in the concentration of NaCl.

Post-hybridization washing

Following hybridization, the preparation is washed to remove any unbound and any non-specifically bound binding partners. The conditions described below are merely by way of example and may depend on the type of preparation to be analysed. During the post-hybridization step, appropriate stringency conditions should be used in order to remove any non-specifically bound binding partner. Stringency refers to the degree to which reaction conditions favour the dissociation of the formed hybrids and may be enhanced, for instance by increasing the washing temperature and incubation time. For conventional hybridization with nucleic acid probes, the salt concentration is often used as an additional factor for regulating the stringency. This does not apply to binding partners comprising polymerized moieties of formula (IV)–(VII), as the binding of this type of probes has been shown to be virtually independent of the salt concentration (Nature, 365, 566–568 (1993)).

Examples of useful buffer systems are Tris-Buffered-Saline (TBS), standard citrate buffer (SSC) or phosphate buffers. A convenient TBS buffer is 0.05M Tris/HCl, 0.15M NaCl, pH 7.6. The SSC buffer comprises 0.15M sodium chloride and 0.015M trisodium citrate, pH 7.0.

Typically, washing times from 25 to 30 minutes may be suitable. Washing periods of two times 10 minutes or 3 times 5 minutes in a suitable buffer may also give good results.

In some cases, particularly when using binding partners carrying at least one fluorescein label, it has been shown to be advantageous to increase the pH of the washing buffer. An increase in the signal-to-noise ratio has been observed using a washing buffer with an alkaline pH. This is apparently due to a significantly reduction of the non-specific binding. In such cases, it is preferred that the washing solution in step (3) has a pH value of from 8 to 10.5, preferably from 9 to 10.

Detection of hybrids formed

In cases where the preparation is deposited onto slides, the hybridization results may be visualized using well known immunohistochemical staining methods to detect the labelling on the binding partner. When fluorescent labelled binding partners are used, the hybrids may be detected using an antibody against the fluorescent label which antibody may be conjugated with an enzyme. The fluorescent label may alternatively be detected directly using a fluorescence microscope, or the results may be automatically analysed on a fluorescent-based image analysis system.

When biotin labelled binding partners are used, the hybrids may be detected using an antibody against the biotin label which antibody may be conjugated with an enzyme. If necessary, an enhancement of the signal can be generated using commercially available amplification systems such as the catalyzed signal amplification system for biotinylated probes (DAKO K 1500).

In the case of a suspended sample such as a cell suspension, quantitative results may be obtained using binding partners comprising a fluorescent label and a flow cytometer to record the intensity of fluorescence per cell.

Binding partners used in some aspects of the present method may form nucleic acid/binding partner hybrids which can be recognized by an antibody described in WO 95/17430. Hybrids formed between the binding partner, nucleic acid and the antibody can be detected in a direct immunohistochemical staining method using, for instance an enzyme conjugated form of the antibody, followed by detection of the enzyme activity or by the application of well known indirect immunohistochemical staining techniques.

ILLUSTRATIVE EMBODIMENTS

To more fully illustrate the present method, the basic aspects of in situ hybridization carried out on tissue sections (A), on cells in suspension (B) or on chromosome spreads (C) are described. While the procedures described are designed for a particular test, the person skilled in the art will comprehend that the principal test procedures may readily be carried out using the appropriate binding partners for the detection of many other specific nucleic acid sequences in samples of eucaryotic origin.

A: Procedure for performing in situ hybridization on tissue sections for the detecting of human papillomavirus (HPV)

Infection with papillomavirus has traditionally been diagnosed using histological staining, electron microscopy or immunohistochemistry designed for the detection of viral antigens. However, these methods are all relatively insensitive. Several different HPV types are known, e.g. HPV types 6, 11, 16, 18, 30, 31, 33, 35, 45, 51, and 52. From these, specific sequences may be selected as the target of detection. By way of example, an in situ hybridization protocol is described for the detection of HPV 16 infected cervical tissue using type specific binding partners.

Step (1): Preparation of sample

A biopsy containing squamous epithelial cells of uterine cervical tissue is treated so as to preserve the morphological integrity of the cellular matrix and of the nucleic acid within the cell. The biopsy is as soon as possible brought to a fixed stage either by means of a chemical fixation or by freezing. A preferred treatment is to use a fixative such as formaldehyde, preferably as a 4% v/v solution in buffer at neutral pH. After fixation for typically from 12 to 14 hours, the biopsy is embedded in paraffin. The paraffin embedded biopsy may be used immediately or may be stored at room temperature for a period of years. From the paraffin embedded biopsy, thin sections having a thickness of typically 3–6 $\mu$m are cut and transferred onto silanized or otherwise adhesive-treated microscope slides.

The slide is then dried, for instance by incubating the slide for 30 minutes at 600° C. in an oven.

The slides are dewaxed, for instance by immersion in a dewaxing solution such as xylene, and rehydrated, e.g. by immersion in 99% ethanol, 95% ethanol, air-drying and immersion into for instance Milli Q water. To increase the accessibility of the target sequences to the binding partner, the tissue section may be treated with a proteolytic agent such as proteinase K. The slides are rinsed in a suitable buffer such as a TBS-buffer.

Step (2): Hybridization

For detecting HPV 16, binding partners comprising polymerized moieties of formula (I)–(VII) can be used. Selection of nucleobases which will be specific for the detection of the HPV 16 is based on public available sequence information retrieved from different databases. One of the most varying regions between the different HPV subtypes are the E6/E7 open reading frame that encodes for two proteins (E6 and E7) involved in the transformation of infected cells. Appropriate binding partners, capable of forming sufficiently stable hybrids with mRNA encoding these proteins, are selected and synthesized.

An appropriate amount of unlabelled or labelled binding partner is brought in contact with the tissue section together with an appropriate hybridization mixture comprising a hybrid destabilizing agent. In a preferred embodiment, the hybridization mixture comprises from 30% to 50% formamide. The tissue section on the slide is incubated at an appropriate temperature for an appropriate period of time. Typically, a binding partner concentration of from 20 to 100 nM, incubation temperatures of from 40° C. to 60° C. and hybridization times of from 10 to 20 minutes are used.

Step (3): Removal of any unbound and any non-specifically bound binding partner

The slides are washed to remove any unbound and any non-specifically bound binding partner. The slides are typically washed in a TBS-buffer at a temperature of from 40° C. to 65° C. for from 15 to 45 minutes. Non-specific binding may be reduced significantly using an alkaline washing buffer. A washing buffer having a pH value from 8 to 10.5 may be employed, preferably from 9 to 10.

Step (4): Detection of hybrids formed

The hybridization results may be visualized using well known immunohistochemical staining methods to detect the labelling on the binding partner. When fluorescent labelled binding partners are used, the hybrids may be detected using an antibody against the fluorescent label which antibody may be conjugated with an enzyme. The fluorescent label may alternatively be detected directly using a fluorescence microscope, or the results may be automatically analysed on a fluorescence-based image analysis system.

When biotin labelled binding partners are used, the hybrids may be detected using an antibody against the biotin label which antibody may be conjugated with an enzyme. If necessary, an enhancement of the signal can be generated using commercially available amplification systems such as the catalyzed signal amplification system for biotinylated probes (DAKO K 1500).

Binding partners used in some aspects of the present method may form nucleic acid/binding partner hybrids which can be recognized by an antibody described in WO 95/17430. Hybrids formed between the binding partner, nucleic acid and the antibody can be detected in a direct immunohistochemical staining method using, for instance an enzyme conjugated form of the antibody, followed by detection of the enzyme activity or by the application of well known indirect immunohistochemical staining techniques.

B: In situ hybridization in suspended preparations for determination of mRNA encoding immunoglobulin Kappa light chain constant region Step (1): Preparation of sample Venous blood is collected into a test tube containing an anticoagulant (e.g. EDTA, citrate or heparin). The mononuclear cells are isolated by centrifugation on a separation medium or, alternatively, the red cells are lysed. The mononuclear cells are washed twice with a synthetic culture medium, RPMI 1640 (Life Technologies), or Phosphate Buffered Saline (PBS). A suitable PBS buffer is 0.01M phosphate, 0.14M NaCl, pH 7.2. The cells are fixed in a fixative such as 70% ethanol (v/v) for 15 minutes at 4° C. A suitable concentration of cells is $10^7$ cells per ml of the fixative.

Step (2): Hybridization

A suspension of cells ($10^5$–$10^6$ cells) is added to 50 µl of preheated hybridization buffer such as Tris/HCl, pH 7.2 comprising suitable amounts of sodium chloride, sodium dodecyl sulphate (SDS), a hybrid destabilizing agent together with a suitable amount of an appropriate binding partner, e.g. binding partner labelled with a fluorescein label, e.g. in a concentration of from 20 to 100 nM. Examples of suitable binding partners are described in Example 1. The test tube is incubated at a suitable temperature, e.g. at a temperature of from 40° C. to 60° C. After 10–30 minutes, the hybridization is stopped by pelleting the cells by centrifugation, e.g. at 8,000 g for 2 minutes.

Step (3): Removal of any unbound and any non-specifically bound binding partner

The cells are washed, e.g. three times for 10 minutes each time at a temperature of from 40° C. to 65° C., in a suitable buffer such as PBS, and subsequently resuspended in a PBS solution (e.g. 500 µl, pH 8.4). The cells are stored refrigerated, e.g. at 4° C., in the dark until analysis.

Step (4): Detection of hybrids formed

Flow cytometry: If a fluorescein labelled binding partner is used, the cells may be monitored on a flow cytometer (e.g. a Becton Dickinson FACScan flow cytometer) equipped with an ion laser device (e.g. an argon ion laser). The laser excitation wavelength of the Becton Dickinson FACScan flow cytometer is 488 nm at 15 mW. The lymphocytes are identified and gated on by measuring forward angle light scatter and right angel light scatter. The green fluorescence of fluorescein is collected through a 530 nm band pass filter. These parameters are acquired as pulse height signals (four decades in logarithmic scale) in list mode for 10,000 events at a rate of approximately 200 cells per second. The data are analysed using LYSYS II software.

Fluorescence microscopy: Deposits of an appropriate number of cells are applied to glass slides and these are sealed with nail varnish and the slides are observed under a fluorescence microscopy. Positive reactions are seen as a fluorescent precipitate.

C: In situ hybridization for the detection of centromeric sequences in chromosomes Step (1): Preparation of sample Metaphase chromosome spreads can be prepared from peripheral blood, bone marrow, amino, chorion villus samples or tumour cells. If prepared from peripheral blood, a sample of whole blood collected in a glass tube containing heparin or another anticoagulant is mixed with suitable growth medium. As an Example, 1 ml whole blood may be added to 8 ml RPMI 1640 medium supplemented with 20% (v/v) foetal calf serum, 2 mM glutamine, 100 U penicillin/streptomycin, 2% phytohemagglutinin and 5 U/ml heparin. The sample is incubated in a $CO_2$ incubator, e.g. at 37° C. for 72 h. The chromosomes are arrested in the metaphase of the mitosis, e.g. by adding colcemid (0.1 µg/ml) to the culture approximately 30 minutes before harvesting the cells.

The cells are collected by centrifugation and resuspended in a hypotonic buffer, e.g. 60 mM KCl at room temperature for about 30 minutes. The sample is treated with a suitable fixative such as methanol:acetic acid 3:1. The treatment with fixative may be repeated several times. The treatment may be performed at freezing temperatures such as at –20° C. of up to 20 minutes. Chromosome spreads are prepared by spotting a suitable amount of the suspension onto a clean and cool slide and air-drying the slide.

Step (2): Hybridization

The binding partners for detecting centromeric sequences may be binding partners comprising polymerized moieties of formula (I)–(VII). Selection of nucleobases specific for centromeric sequences of the chromosomes is based on public available sequence information.

Prior to hybridization, the chromosomal DNA is denatured. Such denaturing may be carried out by placing the slide in a solution of 2×SSC and 70% formamide at about 70° C. for a short period of time such as 2 minutes.

Hybridization may be performed as described above for tissue sections (see step (2) of the description of embodiment A). Dextran sulphate in concentrations of up to 15% can be present during the hybridization, but it is not required.

Alternatively, denaturing and hybridization can be performed simultaneously. If performed simultaneously, it is advantageous to use formamide in a concentration of about 60%.

Step (3): Removal of any unbound and any non-specifically bound binding partner

The slide may be immersed in TBS, pH 7.4, typically at 40° C. to 65° C. for 15 to 45 minutes. Alternatively, the slide may be immersed in a SSC buffer, pH 7.0, containing Triton X-100® such as 0.1×SSC (15 mM NaCl, 1.5 mM sodium citrate pH 7.0) and 0.1% Triton X-100®, typically at 40° C. to 65° C. for 5 to 15 minutes.

Step (4): Detection of hybrids formed

The detection of hybrids formed can be performed as described above for detection of HPV in tissue sections (see step (4) of the description of embodiment A).

In the following examples, special embodiments of the invention are given.

EXAMPLE 1

Comparison between in situ hybridization performed with binding partners of formula (VII) and DNA probes, respectively, for determination of mRNA encoding immunoglobulin Kappa light chain constant region The determination of Kappa light chain expression can be used to detect clonality of lymphoproliferative lesions, for instance to classify patients with multiple myeloma or B cell lymphoma.

To compare the use of binding partners of formula (VII) as hybridization probes with the use of equivalent, but longer, DNA probes, the following experiment was made.
Preparation of samples Samples from normal, human tonsils were fixed for 24 hours in 4% v/v pH neutral buffered formaldehyde. The fixed samples were embedded in paraffin forming a block from which sections having a thickness of from 4 to 5 µm were cut and placed on precoated slides (SuperFrost Plus, Menzel-Gläser, Germany, 041300). The slides were incubated at 65° C. for 60 minutes.

Pretreatment was carried out to unmask tissue mRNA target sequences and to permeabilize the tissue sections for binding partners and detection reagents. The sections were dewaxed and dehydrated through a series of treatments with xylen, 99% ethanol, 95% ethanol and diethylpyrocarbonate-treated, ultrapure water (DEPC-water), respectively. The tissue sections were digested with Proteinase K (DAKO, Denmark, S 3020;1:10 in TBS) in a humid chamber at room temperature for 30 minutes. Following digestion, the slides were washed twice in DEPC-water at room temperature for 5 minutes each time, immersed in 96% v/v ethanol for 10 seconds and air-dried.
Hybridization Binding partners comprising polymerized moieties of formula (VII) were synthesized as described above. For detection of the mRNA encoding Kappa light chain constant region, three binding partners (formulas (VIIa, VIIb, VIIc)) each comprising 15 nucleobases complementary to sequences in the constant region of the Kappa light chain were used. To each binding partner one fluorescein label was attached via linker units L as shown below. The binding partners are written from the N to the C terminal using normal peptide conventions, i.e. H designates a free terminal amino group, and —$NH_2$ designates a terminal carboxamide group. The sequences of the binding partners synthesized were as follows:

Flu-L-L-GAC-TTC-GCA-GGC-GTA-$NH_2$ (VIIa)
Flu-L-L-ACT-TTG-GCC-TCT-CTG-$NH_2$ (VIIb)
Flu-L-L-GAC-AGA-TGG-TGC-AGC-$NH_2$ (VIIc)

wherein Flu denotes a 5-(and 6)-carboxyfluorescein or fluorescein isothiocyanate label, and each L designates a linker unit of the formula —$NH(CH_2CH_2O)_2CH_2C(O)$—.

For hybridization, the binding partners were either used separately or in combination. In any case, the concentration of each of the binding partners was 20 nM (0.1 ng/µl).

DNA probes: DNA oligonucleotides comprising from 25 to 30 nucleotides were selected so as to hybridize to the same regions of the constant region of Kappa light chain mRNA as the above shown binding partners (VIIa)–(VIIc). DNA oligonucleotides were synthesized using an ABI synthesizer, were purified and labelled. Incorporation of Flu-12-dUTP via the enzyme deoxyribonucleotide terminal transferase (TdT, Boehringer Mannheim) resulted in an average labelling of three fluorescein labels per probe. In the hybridization step, the DNA probes were used separately or in combination, in either case in a concentration of 12 nM (0.1 ng/µL).

The air-dried tissue sections on the slides were each covered with 15 µl hybridization solution. The hybridization solution consisted of 10 mM NaCl (0.6M NaCl for the DNA probes) (Merck, Germany, 6404.5000), 10% dextran sulphate w/v (Sigma U.S.A., D-8906), 30% formamide v/v (Life Technologies, U.S.A., 55150B), 0.1% sodium pyrophosphate, 0.2% polyvinylpyrrolidone (MW 40000), 0.2% ficoll (MW 400000), 5 mM $Na_2$ EDTA, 0.05M Tris/HCl, pH 7.5 and the respective binding partners in the above-indicated concentrations. The sections were covered with coverslips in order to ensure even distribution of the hybridization solution and they were incubated in the dark in a humid chamber at 37° C. for 1.5 h.
Removal of any unbound and any non-specifically bound binding partner Following the hybridization, the coverslip and hybridization solution were removed and the slides were transferred to a jar containing TBS at pH 7.6 and kept at room temperature. The slides were washed 3×3 minutes and the buffer was renewed between each wash.
Detection of hybrids formed Following the post-hybridization wash, the slides were immersed in TBS at room temperature. A ready-to-use Rabbit (Fab) anti-FITC/AP conjugate (DAKO K0076) was used to detect the hybrids formed. The slides were incubated for 30 minutes with the antibody in a humid chamber at room temperature. After incubation, the antibody was tapped off and the slides were washed twice in TBS, each time for 3 minutes, followed by two washes in Milli-Q water, each time for 1 minutes. The alkaline phosphatase bound via the antibody was monitored by addition of BCIP/NBT substrate 1:50 at pH 9.0 (DAKO K0046) and the slides were incubated in a humid chamber at room temperature for 1 hour (BCIP is 5-bromo-4-chloro-3-indolyl phosphate and NBT is nitroblue tetrazolium). Finally, the slides were washed in tap water and mounted using Glycergel (DAKO, C 0563)
Conclusion Hybridization, i.e. positive stainings, was recognized under the microscope as a dark blue/black colour. It appeared that the signal obtained with the separate or combined binding partners (VIIa)–(VIIc) was stronger than the signal obtained with the equivalent separate or combined DNA probes even though fewer detection molecules were available on the binding partners (VIIa)–(VIIc) (only one label on each of the binding partners (VIIa)–(VIIc) as compared to an average of three labels on each of the DNA probes). Non-specific binding was observed when using the binding partners (VIIa)–(VIIc), particularly when the three binding partners were used in combination.

In contrast to hybridization between two nucleic acid strands, the hybridization between binding partners comprising polymerized moieties of formula (VII) and a target nucleic acid appears to be insensitive to the salt concentration. No difference in ratio between specific and non-specific binding was observed in an experiment using 0.01M, 0.1M or 0.6M NaCl in the hybridization solutions. Furthermore, no difference was seen when the pH value of the hybridization solution was changed from 7.6 to 9.0 or 10.0.

EXAMPLE 2

Effect of variation of the concentration of binding partner, of the hybridization and washing temperatures and times on hybridization in the detection of sequences in the Kappa light chain constant region
Preparation of samples Sections of normal, human tonsils were prepared as described in Example 1.
Hybridization The three binding partners mentioned in Example 1 were used separately or in combination. The binding partners (VIIa)–(VIIc) were used in a hybridization solution as described in Example 1 with the exception that the concentration of each binding partner was 20, 50, or 100 nM, respectively. Incubations were made for 1½ hour at 37° C., 45° C., 50° C., 55° C. or 60° C., respectively.
Removal of any unbound and any non-specifically bound binding partner Post-hybridization washes were performed in TBS pH 7.6 for 25 minutes at the same temperature as for the hybridization, namely at 37° C., 45° C., 50° C., 55° C. or 60° C., respectively.
Detection of hybrids formed
As described in Example 1.
Conclusions
The results indicated that no improvement regarding the signal-to-noise ratio was obtained when using concentrations of binding partners (VIIa)–(VIIc) higher than 20 nM. This was due to a simultaneous increase in non-specific binding. Increased temperature during hybridization and post-hybridization wash lowered the non-specific binding without reducing the specific binding. The decrease in non-specific binding was most clearly observed when the binding partners (VIIa)–(VIIc) were used in combination. The highest signal-to-noise ratio was obtained using each of the three binding partners (VIIa)–(VIIc) separately in a concentration of 20 nM and performing hybridization and wash at a temperature of 55° C. No significant difference was observed for the individual binding partners.

EXAMPLE 3

Effect of variations of the post-hybridization washing solution on the binding of binding partners in the detection of sequences in the Kappa light chain constant region To further investigate the nature of the binding of the three binding partners (VIIa)–(VIIc), a variety of post-hybridization washing solutions was made.
Preparation of samples
Sections of normal, human tonsils were prepared as described in Example 1.
Hybridization
The hybridization conditions were identical to the conditions described in Example 1 with the exception that the hybridization temperature was 55° C. A combination of the three binding partners described in Example 1 was used, each at a concentration of 20 nM.
Removal of any unbound and any non-specifically bound binding partner
The post-hybridization wash was carried out using the solutions shown in Table 1. The wash was carried out for 25 minutes at 55° C. with gentle shaking.
Detection of hybrids formed
As described in Example 1.
The results are shown in Table 1.

TABLE 1

| Post-hybridization solution | Specific binding | Non-specific binding |
| --- | --- | --- |
| 0.05 M TBS, pH 7.6 | +++(+) | ++ |
| 0.05 M TBS, pH 9.1 | +++(+) | + |
| 0.05 M TBS, pH 9.5 | +++(+) | (+) |
| 0.05 M TBS, pH 10.0 | +++ | – |
| 0.05 M TBS, pH 10.5 | (+) | – |
| 0.05 M TBS, pH 11.0 | – | – |

With respect to the specific binding (specific staining), the scoring-system used for evaluation was as follows: ++++; +++(+); +++; ++(+); ++; +(+); + and (+), where ++++ through (+) designate a scoring from intense specific stained cells through faint or few specific stained cells. A scoring indicated as – designates no staining.

With respect to the non-specific binding (background staining), the scoring-system used for evaluation was as follows: ++; +(+); + and (+), where ++ through (+) designate a scoring from homogeneous staining of cells and intercellular matrix, which makes evaluation of faint positive cells difficult, through faint homogenous staining of cells and intercellular matrix. A scoring indicated as – designates no background staining (no non-specific binding).
Conclusion
The results show that the use of TBS-containing post-hybridization wash solutions with a pH from about 9 to 10 results in a significant decrease of the non-specific binding without compromising the intensity of the specific binding significantly. Even using high concentration of binding partner, e.g. 50 nM, the non-specific binding described in Example 1 decrease significantly when using an alkaline washing buffer (see Example 6).

EXAMPLE 4

Influence of different hybrid destabilizing agents on hybridization in the detection of sequences in the Kappa light chain constant region
Preparation of samples
Sections of normal, human tonsils were prepared as described in Example 1.
Hybridization
Hybridization conditions as described in Example 1 with the exception that the hybrid destabilizing agent was varied. Three different hybrid destabilizing agents were used, namely formamide, ethylene glycol and glycerol. A combination of the three binding partners (VIIa)–(VIIc) from Example 1 was used, and hybridization was carried out for 60 minutes at 55° C. The concentration of each of the binding partners was 20 nM.
Removal of any unbound and any non-specifically bound binding partner
The slides were washed in TBS buffer at pH 10 at 55° C. The washing time was 25 minutes.
Detection of hybrids formed
As described in Example 1.
The results obtained are given in Table 2. The scoring system are as described in Example 3; nd denotes not determined. In all experiments, only negligible non-specific binding was observed.

TABLE 2

| % hydrid destabilizing agent | Specific binding Formamide | Specific binding Ethylene glycol | Specific binding Glycerol |
| --- | --- | --- | --- |
| 10 | nd. | nd. | – |
| 20 | ++ | (+) | nd. |
| 25 | nd. | nd. | – |
| 30 | +++ | (+) | nd. |
| 40 | ++++ | + | nd. |
| 50 | +++ | +++ | ++(+) |
| 60 | +++ | +++ | nd. |
| 64.8 | nd. | ++++ | nd. |

EXAMPLE 5

Variation of both hybrid destabilizing agent and hybridization time in the detection of sequences in the Kappa light chain constant region
Preparation of samples
Sections of normal, human tonsils were prepared as described in Example 1.
Hybridization
Hybridization conditions as described in Example 4 with the exception that the following concentrations of the hybrid destabilizing agent were used: formamide, 30%; ethylene glycol, 65% and glycerol, 50%. Hybridization times 15, 30, and 60 minutes, respectively.

Removal of any unbound and any non-specifically bound binding partner

The slides were washed in TBS buffer at pH 10 at 55° C. and the washing time was 25 minutes.

Detection of hybrids formed

As described in Example 1.

The results obtained are given in Table 3. Definition of the scoring-system is given in Example 3. In all experiments, only negligible non-specific binding was observed.

TABLE 3

| Hybridization time (minutes) | Specific binding Formamide | Specific binding Ethylene glycol | Specific binding Glycerol |
|---|---|---|---|
| 15 | +++ | − | − |
| 30 | +++ | +(+) | + |
| 60 | +++ | ++(+) | ++ |

Conclusion

The results indicate that longer hybridization times are necessary when ethylene glycol or glycerol is used as hybrid destabilizing agent as compared to those of formamide.

EXAMPLE 6

Effect of variation of pH of a TBS post-hybridization washing solution on the hybridization of binding partners to sequences in the Kappa light chain constant region Preparation of samples Sections of normal, human tonsils were prepared as described in Examples 1.

Hybridization

Binding partners of formulas (VIIa)–(VIIf) comprising polymerized moieties of formula (VII) were synthesized as described above. The binding partners comprised 15 nucleobases complementary to sequences in the constant region of the Kappa light chain. The sequences of the binding partners synthesized were as follows:

Flu-L-L-GAC-TTC-GCA-GGC-GTA-NH$_2$ (VIIa)

Flu-L-L-ACT-TTG-GCC-TCT-CTG-NH$_2$ (VIIb)

Flu-L-L-GAC-AGA-TGG-TGC-AGC-NH$_2$ (VIIc)

Flu-L-L-GAC-TTC-GCA-GGC-GTA-L-Flu (VIId)

Flu-Lys(Flu)-L-GAC-TTC-GCA-GGC-GTA-NH$_2$ (VIIe)

Flu-Lys(Flu)-L-GAC-AGA-TGG-TGC-AGC-NH$_2$ (VIIf)

wherein Flu denotes a 5-(and 6)-carboxyfluorescein or fluorescein isothiocyanate label, Lys designates lysine label and each L designates a linker unit of the formula —NH(CH$_2$CH$_2$O)$_2$CH$_2$C(O)—.

Hybridization conditions were as described in Example 1 with the exception that the hybridization temperature was 55° C. Binding partners (VIIa), (VIIc), (VIId), (VIIe) and (VIIf) were used separately or binding partners (VIIa), (VIIb) and (VIIc) were used in combination. The concentration of each binding partner was 20 nM (Table 4 A) and 50 nM (Table 4 B), respectively.

Removal of any unbound and any non-specifically bound binding partner

Post-hybridization wash was carried out in a TBS-buffer at pH 7.6, 9.0 or 10.0 for 25 minutes at 55° C.

The results are given in Tables 4 A and 4 B. The scoring-system used is described in Example 3.

TABLE 4A

| | ph of washing buffer | | | | | |
|---|---|---|---|---|---|---|
| | 7.6 | | 9.0 | | 10.0 | |
| Binding partner (20 nM of each) | Specific binding | Non-specific binding | Specific binding | Non-specific binding | Specific binding | Non-specific binding |
| Combination of (VIIa), (VIIb) and (VIIc) | +++(+) | ++ | +++(+) | + | +++ | − |
| (VIIa) | ++(+) | + | ++ | (+) | ++ | − |
| (VIId) | +++ | (+) | +++ | (+) | ++(+) | − |
| (VIIe) | +++ | (+) | +++ | − | ++(+) | − |
| (VIIc) | ++ | + | ++ | − | ++(+) | − |
| (VIIf) | +++ | +(+) | +++ | + | ++(+) | (+) |

TABLE 4B

| | ph of washing buffer | | | | | |
|---|---|---|---|---|---|---|
| | 7.6 | | 9.0 | | 10.0 | |
| Binding partner (50 nM of each) | Specific binding | Non-specific binding | Specific binding | Non-specific binding | Specific binding | Non-specific binding |
| Combination of (VIIa), (VIIb) and (VIIc) | +++ | ++ | +++ | + | +++ | (+) |
| (VIIa) | ++(+) | +(+) | ++(+) | + | ++ | − |
| (VIId) | +++ | +(+) | +++ | (+) | ++(+) | (+) |
| (VIIe) | +++ | +(+) | ++ | (+) | ++(+) | − |
| (VIIc) | ++(+) | +(+) | ++ | + | ++ | − |
| (VIIf) | +++(+) | ++ | +++ | +(+) | +++ | (+) |

Conclusion

The results indicate that the non-specific binding can be removed by using a washing solution with increased pH compared to a pH of 7.6 without decreasing the specific binding significantly.

EXAMPLE 7

Effect of variation of formamide concentration on the hybridization performance in the detection of sequences in the Kappa light chain constant region Preparation of samples Sections of normal, human tonsils were prepared as described in Example 1.

Hybridization

The following binding partners comprising moieties of formula (VII) were used: Flu-L-L-GAC-TTC-GCA-GGC-GTA-NH$_2$ (VIIa) or Bio-L-L-GAC-TTC-GCA-GGC-GTA-NH$_2$ (VIIg), wherein Flu denotes a 5-(and 6)-carboxyfluorescein or fluorescein isothiocyanate label, Bio denotes a biotin label and each L denotes a linker unit of the formula —NH(CH$_2$CH$_2$O)$_2$CH$_2$C(O)—.

The hybridization solution was identical to the solution described in Example 1 with the exception that the formamide concentration was varied from 0 to 60% and that the concentration of the binding partner (VIIa) or (VIIg) was 50 nM. The slides were incubated in a humid chamber in the dark at 55° C. for 1.5 hours.

Removal of any unbound and any non-specifically bound binding partner

The post-hybridization wash was carried out in a TBS-solution at pH 10 for 25 minutes at 55° C. under gentle shaking.

Detection of hybrids formed

Detection of hybrids formed with the fluorescein-labelled binding partner (VIIa) was carried out as described in Example 1. Detection of hybrids formed with the biotin-labelled binding partner (VIIg) was carried out using streptavidin/alkaline phosphatase (DAKO D396 1:100). Following incubation for 30 minutes at room temperature, the slides were rinsed and the activity of alkaline phosphatase was monitored by addition of BCIP/NBT substrate as described in Example 1. The results are shown in Table 5. Definition of the scoring-system is given in Example 3.

TABLE 5

| Formamide concentration (%) | Flu-labelled binding partner (VIIa) | | Bio-labeled binding partner (VIIg) | |
| --- | --- | --- | --- | --- |
| | Specific binding | Non-specific binding | Specific binding | Non-specific binding |
| 0 | − | − | − | + |
| 5 | − | − | (+) | + |
| 11 | (+) | − | (+) | + |
| 15 | (+) | (+) | (+) | + |
| 20 | + | (+) | ++ | + |
| 30 | ++(+) | (+) | +++ | + |
| 40 | +++ | (+) | ++(+) | + |
| 50 | +++ | (+) | + | + |
| 60 | +(+) | (+) | (+) | + |

Conclusion

Form the results, it may be concluded that, for the binding partners used in this experiment and the applied hybridization and post-hybridization wash conditions, a concentration of at least 10–15% formamide seems to be necessary in order to obtain specific binding. In this experiment, a concentration of 30–50% formamide seemed to give the best signal-to-noise ratio.

Using other binding partners comprising polymerized moieties of formula (VII), e.g. binding partners directed against the EBV encoded EBER nuclear RNA's, acceptable results have been obtained without any formamide in the hybridization solution, but the best results were still achieved with 30–40% formamide in the hybridization buffer (results not shown).

EXAMPLE 8

Variation of hybridization time and concentration of binding partner at alkaline washing pH and a temperature of 55° C. in the detection of sequences in the Kappa light chain constant region Preparation of samples Sections of normal, human tonsils were prepared as described in Example 1.

Hybridization

The hybridization was carried out as described in Example 1 with the exception that the hybridization time was varied from 5 to 90 minutes and that the hybridization temperature was kept at 55° C. A combination of the three binding partners (VIIa)–(VIIc) described in Example 1 was used. The concentration of each of the binding partners was 6, 12, 25 or 50 nM.

Removal of any unbound and any non-specifically bound binding partner

The slides were washed for 25 minutes in a TBS buffer at pH 10. The washing temperature was 55° C.

Detection of hybrids formed

As described in Example 1.

The results are given in Tables 6 A and 6 B. Definition of the scoring-system is given in Example 3.

TABLE 6

| | Binding partner concentration | | | |
| --- | --- | --- | --- | --- |
| Hybridization | 50 nM (of each) | | 25 nM (of each) | |
| time (minutes) | Specific binding | Non-specific binding | Specific binding | Non-specific binding |
| 5 | ++++ | − | +++(+) | − |
| 15 | ++++ | − | +++(+) | − |
| 30 | +++ | − | +(+) | − |
| 45 | ++++ | (+) | ++++ | (+) |
| 60 | ++++ | (+) | +++(+) | (+) |
| 90 | ++++ | + | +++(+) | + |

TABLE 6B

| | Binding partner concentration | | | |
| --- | --- | --- | --- | --- |
| Hybridization | 12 nM (of each) | | 6 nM (of each) | |
| time (minutes) | Specific binding | Non-specific binding | Specific binding | Non-specific binding |
| 5 | +++ | − | ++(+) | − |
| 15 | +++ | − | ++(+) | − |
| 30 | +++(+) | − | +++ | − |
| 45 | +++(+) | (+) | +++ | − |
| 60 | +++(+) | (+) | +++(+) | (+) |
| 90 | +++(+) | + | +++ | (+) |

Conclusion

The results indicate that if hybridization was carried out for a period of from 5 minutes to 30 minutes, non-specific binding was not observed. It is very remarkable that a high scoring for specific binding was obtained even with the very short hybridization time of 5 minutes. It appears that this scoring was only slightly reduced when the concentration of the binding partner was reduced from 50 through 6 nM. However, a faint homogeneous non-specific binding to cells and intercellular matrix (scoring (+)) is obtained with hybridization times longer than 45 minutes. The results shown in Tables 6 A and 6 B indicate that the present method is very flexible with regard to several parameters, which indeed makes the method very suitable for both quick screening as well as for being part of a larger set-up of tests where longer hybridization times may be more convenient.

EXAMPLE 9

Short hybridization time and variation of washing times in the detection of sequences in the Kappa light chain constant region Preparation of samples Sections of normal, human tonsils were prepared as described in Example 1.

Hybridization

Hybridization conditions were as described in Example 1 with the exception that the hybridization time was 15 minutes and the hybridization temperature was 55° C. The three binding partners described in Example 1, (VIIa)–(VIIc), were used in combination. The concentration of each of the binding partners was 50 nM.

Removal of any unbound and any non-specifically bound binding partner

The slides were washed in a TBS buffer at pH 10 at 55° C. and the wash was carried out the three following ways: 1×25 minutes, 2×10 minutes or 3×5 minutes, respectively.

Detection of hybrids formed

As described in example 1.

The results are given in Table 7. The scoring-system is as defined in Example 3.

TABLE 7

| Washing times (minutes) | Specific binding | Non-specific binding |
|---|---|---|
| 25 | ++++ | – |
| 2 × 10 | ++++ | – |
| 3 × 5 | ++++ | – |

EXAMPLE 10

Detection of sequences in the Kappa light chain constant region using variable amount of dextran sulphate Preparation of samples Sections of normal human tonsils were prepared as described in Example 1.

Hybridization

Binding partners of formulas (VIIa), (VIIb), (VIIc) or (VIIm) comprising polymerized moieties of formula (VII) were synthesized as described above. The binding partners used comprised 15 nucleobases complementary to sequences in the Kappa light chain. The sequence of the binding partners were as follows:

Flu-L-L-GAC-TTC-GCA-GGC-GTA-NH$_2$ (VIIa)

Flu-L-L-ACT-TTG-GCC-TCT-CTG-NH$_2$ (VIIb)

Flu-L-L-GAC-AGA-TGG-TGC-AGC-NH$_2$ and (VIIc)

Flu-L-L-GAC-TTC-GCA-GGC-GTA-L-L-Flu (VIIm)

wherein Flu denotes a 5-(and 6)-carboxyfluorescein or fluorescein isothiocyanate label and each L designates a linker unit of the formula —NH(CH$_2$CH$_2$O)$_2$CH$_2$(O)—.

Binding partners (VIIa), (VIIb) and (VIIc) were used in combination, and binding partner (VIIm) were used separately. The concentration of each binding partner was 50 nM or 20 nM, respectively. The hybridization solution used was as described in Example 1 with the exception that it contained either 0% or 10% dextran sulphate. The hybridization was performed at 55° C. for 90 minutes.

Removal of any unbound and any non-specifically bound binding partner

The post-hybridization wash was performed in a TBS buffer at pH 10.0 for 25 minutes.

Detection of hybrids formed

The detection of hybrids formed was carried out as described in Example 1. The results are shown below in Tables 8A (results obtained with a combination of binding partners (VIIa), (VIIb) and (VIIc)) and 8B (results obtained with binding partner (VIIm)) below. Definition of the scoring system is given in Example 3.

TABLE 8A

| Concentration of binding partner | Specific binding (10% dextran sulphate) | Specific binding (0% dextran sulphate) |
|---|---|---|
| Combination of (VIIa), (VIIb) and (VIIc), 20 nM | ++(+) | – |
| Combination of (VIIa), (VIIb) and (VIIc), 50 nM | +++ | (+) |

TABLE 8B

| Concentration of binding partner | Specific binding (10% dextran sulphate) | Specific binding (0% dextran sulphate) |
|---|---|---|
| (VIIm), 20 nM | ++ | – |
| (VIIm), 50 nM | +++ | – |

EXAMPLE 11

Detection of sequences in the Kappa light chain constant region using variable amount of dextran sulphate Preparation of samples Sections of normal human tonsils were prepared as described in Example 1.

Hybridization

Binding partners of formulas (VIIa), (VIIb) and (VIIm) comprising polymerized moieties of formula (VII) were synthesized as described above. The binding partners used comprised 15 nucleobases complementary to sequences in the Kappa light chain. The sequences of the binding partners were as follows:

Flu-L-L-GAC-TTC-GCA-GGC-GTA-NH$_2$ (VIIa)

Flu-L-L-ACT-TTG-GCC-TCT-CTG-NH$_2$ and (VIIb)

Flu-L-L-GAC-TTC-GCA-GGC-GTA-L-L-Flu (VIIm)

wherein Flu denotes a 5-(and 6)-carboxyfluorescein or fluorescein isothiocyanate label and each L designates a linker unit of the formula —NH(CH$_2$CH$_2$O)$_2$CH$_2$(O)—.

The binding partners were used in combination, and the concentration of each binding partner was 20 nM. The hybridization solution used was as described in Example 1 with the exception that the hybridization solution contained either no dextran sulphate or 2.5%, 5%, 7.5%, 10%, 12.5% or 15% dextran sulphate, respectively.

Removal of any unbound and any non-specifically bound binding partner

The post-hybridization wash was performed in a TBS buffer at pH 7.6 or at pH 10.0 for 25 minutes.

Detection of hybrids formed

The detection of hybrids formed was carried out as described in Example 1. The results are shown below in Tables 9A (results obtained using a TBS buffer at pH 7.6 as post-hybridization washing buffer) and 9B (results obtained using a TBS buffer at pH 10.0 as post-hybridization washing buffer) below. Definition of the scoring system is given in Example 3.

TABLE 9A

| Concentration of dextran sulphate (TBS, pH 7.6) | Specific binding | Non-specific binding |
|---|---|---|
| 0% | (+) | – |
| 2.5% | +++(+) | ++(+) |
| 5% | +++(+) | ++(+) |
| 7.5% | +++ | + |
| 10% | +++(+) | ++ |
| 12.5% | +++(+) | ++ |
| 15% | +++(+) | ++(+) |

TABLE 9B

| Concentration of dextran sulphate (TBS, pH 10.0) | Specific binding | Non-specific binding |
|---|---|---|
| 0% | (+) | – |
| 2.5% | +++ | – |
| 5% | +++ | – |
| 7.5% | ++ | – |
| 10% | +++(+) | – |
| 12.5% | +++(+) | – |
| 15% | +++(+) | – |

EXAMPLE 12

Detection of *Chlamydia trachomatis* using in situ hybridization

Clinical samples of eucaryotic origin are often infected with different bacteria or virus. For instance, may samples from the urethra or cervix be infected with *C. trachomatis* or *Neisseria gonorrhoea*. Binding partners directed against 16S and 23S ribosomal RNA from *C. trachomatis* were selected and synthesized. The binding partners were labelled with one fluorescein label.

Preparation of samples

Infection of the mouse cell-line L929 with the $L_1$ strain of *C. trachomatis* was performed by standard techniques. Cells containing "whole cell inclusions" were smeared onto glass microscope slides. The sample preparation was fixed in acetone for 10 minutes, air-dried and used for subsequent in situ hybridization. Slides prepared in a similar manner, but containing smears of cells infected with *C. pneumoniae* were used to test the specificity of the binding partners.

Hybridization

Binding partners were synthesized of which one was directed against *C. trachomatis* 16S ribosomal RNA (VIIh) and three were directed against 23S ribosomal RNA ((VIIi), (VIIj) and (VIIk)). The binding partners were all labelled with one fluorescein label as shown below. The sequences are given below:

Flu-L-AAC-GTT-ACT-CGG-ATG-$NH_2$ (VIIh)

Flu-L-GTC-TTT-GCT-TAT-CAC-$NH_2$ (VIIi)

Flu-L-L-TGT-CGC-TTT-GCA-TAC-$NH_2$ (VIIj)

Flu-L-L-CCT-TTA-TCC-TCA-ATC-$NH_2$ (VIIk)

wherein Flu denotes a 5-(and 6)-carboxyfluorecein or fluorescein isothiocyanate label, and each L denotes a linker unit of the formula —$NH(CH_2CH_2O)_2CH_2C(O)$—.

The binding partners were used separately or in combination. The hybridization solution used is described in Example 1 with the exception that 0.1% Triton X-100® was added and that the concentration of each of the binding partners was 100 or 500 nM. The hybridization was performed at 55° C. for 90 minutes.

Removal of any unbound and any non-specifically bound binding partner

The slides were washed in TBS buffer at pH 7.6 at 55° C. for 25 minutes.

Detection of hybrids formed

The slides were mounted using a mounting media suited for fluorescent detection and were examined by fluorescent microscopy.

The results are given in Table 10. Definition of the scoring-system is given in Example 3.

TABLE 10

| | Scoring of fluorescence C. trachomatis | | Scoring of fluorescence C. pneumoniae | |
|---|---|---|---|---|
| Binding partner | 100 nM | 500 nM | 100 nM | 500 nM |
| (VIIh) | ++(+) | +(+) | – | – |
| (VIIi) | + | ++ | – | – |
| (VIIj) | +(+) | ++(+) | – | – |
| (VIIk) | +(+) | ++ | – | – |
| Combination of (VIIh), (VIIi), (VIIj) and (VIIk) | +++ | +++(+) | – | – |

Conclusion

As can be seen from the results, the binding partners hybridized to *C. trachomatis* but not to *C. pneumoniae*. It can also be seen that the specific binding is enhanced when the binding partners are used in combination (VIIh)–(VIIk). Furthermore, no non-specific binding was observed.

EXAMPLE 13

Detection of *Chlamydia trachomatis* using a variable amount of dextran sulphate Preparation of samples Smears of cells containing "whole cell inclusions" of *C. trachomatis* were prepared as described in Example 12.

Hybridization

The four binding partners, (VIIh)–(VIIk), as described in Example 12 were used in combination.

The hybridization solution used was as described in Example 1 with the exception that it further contained 0.1% Triton X-100®. Furthermore, the hybridization solution contained either 0% or 10% dextran sulphate. The concentration of each of the binding partners was 100 or 500 nM, respectively. The hybridization was performed at 55° C. for 90 minutes.

Removal of any unbound and any non-specifically bound binding partner

The slides were washed in TBS buffer at pH 7.6 at 55° C. for 25 minutes.

Detection of hybrids formed

The slides were mounted using a mounting media suited for fluorescent detection and were examined by fluorescent microscopy.

The results are given in Table 11 below.

TABLE 11

| Concentration of binding partner | Specific binding (10% dextran sulphate) | Specific binding (0% dextran sulphate) |
|---|---|---|
| Combination of (VIIh), (VIIi), (VIIj) and (VIIk), 100 nM | +(+) | – |
| Combination of (VIIh), (VIIi), (VIIj) and (VIIk), 500 nM | ++(+) | – |

EXAMPLE 14
Detection of *Neisseria gonorrhoea* in clinical samples
Preparation of samples Swabs were taken from the urethra or cervix of eight patients suffering from a *N. gonorrhoea* infection. The samples were evaluated as positive on the basis of methylene blue and/or Gram staining.

Smears of the samples were prepared on glass microscope slides and subsequently fixed by flame fixation.
Hybridization Binding partners of formulas (VIIn) and (VIIp) comprising polymerized moieties of formula (VII) were synthesized as described above. The binding partners comprised 15 nucleobases complementary to 16S ribosomal *Neisseria gonorrhoea* RNA, and were as follows:

Flu-L-L-CCC-CGC-TAC-CCG-GTA-$NH_2$ (VIIn)

Flu-L-L-CGC-ACA-TGT-CAA-AAC-$NH_2$ (VIIp)

wherein Flu denotes a 5-(and 6)-carboxyfluorescein or fluorescein isothiocyanate label, and L designates a linker unit of the formula —$NH(CH_2CH_2O)_2CH_2C(O)$—.

The binding partners were used in combination. The concentration of each binding partner was 500 nM. The hybridization solution used was as described in Example 1 with the exception that the solution further contained 0.1% Triton X-100®. The hybridization was performed at 55° C. for 90 minutes.
Removal of any unbound and any non-specifically bound binding partner The post-hybridization wash was performed in a TBS buffer at pH 7.6 for 25 minutes.
Detection of hybrids formed The slides were mounted using a mounting media suited for fluorescent detection and were examined by fluorescent microscopy.
Conclusion Seven of the eight samples were clearly positive in that cells of *N. gonorrhoea* could easily been identified. Furthermore, in six of these seven samples, typical diplococci were observed distinctly intracellularly in the granolucytes. One sample was negative when tested by this method.

EXAMPLE 15
Detection of *Neisseria gonorrhoea* using variable amount of dextran sulphate
Preparation of samples Smears of samples were prepared as described in Example 14.
Hybridization Binding partners of formulas (VIIn), (VIIo) and (VIIp) comprising polymerized moieties of formula (VII) were synthesized as described above. The binding partners comprised 15 nucleobases in a sequence complementary to 16S *N. gonorrhoea* ribosomal RNA. The sequence of the binding partners were as follows:

Flu-L-L-CCC-CGC-TAC-CCG-GTA-$NH_2$ (VIIn)

Flu-L-L-CCC-CGC-CAA-CCA-GCT-$NH_2$ (VIIo)

Flu-L-L-CGC-ACA-TGT-CAA-AAC-$NH_2$ (VIIp)

wherein Flu denotes a 5-(and 6)-carboxyfluorescein or fluorescein isothiocyanate label, and L designates a linker unit of the formula —$NH(CH_2CH_2O)_2CH_2C(O)$—.

The binding partners were used in combination, and the concentration of each binding partner was 100 nM. The hybridization solution used was as described in Example 1 with the exception that the solution was added 0.1% Triton X-100® and that the content of dextran sulphate was either 0% or 10%. The hybridization was performed at 55° C. for 90 minutes.

Removal of any unbound and any non-specifically bound binding partner

The post-hybridization wash was performed in a TBS buffer at pH 7.6 for 25 minutes.
Detection of hybrids formed The slides were mounted using a mounting media suited for fluorescent detection and were examined by fluorescent microscopy.

The obtained results are shown in Table 12 below.

TABLE 12

| Concentration of binding partner | Specific binding (10% dextran sulphate) | Specific binding (0% dextran sulphate) |
|---|---|---|
| Combination of (VIIn), (VIIo) and (VIIp) 100 nM | ++(+) | +(+) |

EXAMPLE 16
Flow cytometric detection of EBV in a suspended preparation using in situ hybridization
Preparation of samples Freshly harvested EBV infected HS-Sultan cells ($5 \times 10^7$ cells/ml) or not infected CEM T cells (negative control; $5 \times 10^7$ cells/ml) were fixed in 1% paraformaldehyde for 15 minutes at room temperature (RT). The cell suspension was centrifuged at 340×g for 5 minutes. The supernatant was removed, and to block endogenous RNAse activity, the cell pellet was resuspended in 2.5 ml 70% ethanol to which 10 µl 10% diethyl-pyrocarbonate (DEPC) had been added (10% DEPC was prepared in 70% ethanol). The cell suspension was incubated at RT for 15 minutes, followed by centrifugation at 340×g for 5 minutes. The supernatant was removed and the cell pellet was resuspended in 70% ethanol/DEPC. The suspended preparation was stored at −20° C. if not used immediately for in situ hybridization.

For in situ hybridization, 100 µl of the suspended preparation was mixed with 1 ml TBS. The suspension was centrifuged at 340×g for 5 minutes, the supernatant was removed and the pellet was resuspended in 0.5 ml TBS containing 5 µl Proteinase K (DAKO, S3020). The suspension was incubated for 10 minutes at 37° C. To the cell suspension, 1 ml TBS was added, and the suspension was centrifuged at 340×g for 5 minutes. The supernatant was removed, and the cell pellet was resuspended in 1 ml TBS. After centrifugation at 340×g for 5 minutes the supernatant was removed, and the cell pellet was resuspended in 100 µl TBS. This cell suspension was subjected to a prehybridization treatment with the hybridization solution but without binding partner (100 µl suspension was mixed with 0.5 ml of hybridization solution containing 30% formamide, 1×TBST, 5% dextran sulphate (TBST is TBS containing 0.1% Triton X-100)). The supernatant was removed after centrifugation at 700×g for 5 minutes, and the pellet was used for hybridization.
Hybridization A binding partner of formula (VIIs) comprising polymerized moieties of formula (VII) was used for hybridization. The binding partner comprised 15 nucleobases complementary to a sequence in EBV encoded EBER nuclear RNA. The sequence of the binding partner was as follows:

Bio-L-L-CCT-CTA-GGG-CAG-CGT-L-Lys-Bio (VIIs)

wherein Bio denotes a biotin label, Lys designates a lysine peptide label, and each L designates a linker unit of the formula —$NH(CH_2CH_2O)_2CH_2C(O)$—.

Hybridization was performed by resuspending the pellet obtained above in 65 µl of a mixture of 30% formamide, 1×TBST, 5% dextran sulphate and 500 nM of binding partner (VIIs). The sample was incubated for 1.5 h at 55° C. (waterbath).

Removal of any unbound and any non-specifically bound binding partner

Following the hybridization, 1 ml TBST heated to 55° C. was added and the sample was centrifuged at 700×g. The supernatant was removed, the pellet was resuspended in 1 ml TBST heated to 55° C. and the sample was incubated for 45 minutes at 55° C. The sample was centrifuged at 700×g for 5 minutes, the supernatant was removed and the pellet was used in the detection step.

Detection of hybrids formed

The pellet obtained above was resuspended in 100 μl Steptavidin/FITC (DAKO, F0422) diluted 1:50 in 1% BSA (bovine serum albumin) in TBST. The sample was incubated in the dark for 30 minutes at RT. Following incubation, 2 ml TBST was added and the sample was centrifuged at 700×g for 5 minutes. The supernatant was removed and the pellet was resuspended in 0.5 ml TBST and analyzed on a Becton Dickinson FACSort instrument.

Conclusion

With the above described procedure, a FITC-fluorescence ratio of 5.79 on a 4 decade logarithmic scale was observed between the EBV positive cells and the EBV negative CEM cells.

EXAMPLE 17

In situ hybridization for the detection of X chromosome specific sequences in chromosome metaphase spreads Detection of centromer specific sequences can be used to determine numerical aberrations of chromosomes in, e.g., prenatal diagnosis or tumour diagnosis.

Preparation of samples

Metaphase chromosome spreads were prepared from peripheral blood. 1 ml of female whole blood was added to 8 ml RPMI 1640 medium supplemented with 20% (v/v) foetal calf serum, 2 mM glutamine, 100 U penicillin/streptomycin, 2% phyto-hemagglutinin and 5 U/ml heparin in a glass tube. The sample was incubated in a $CO_2$ incubator at 37° C. for 72 hours. The chromosomes were arrested in the meta-phase of the mitosis by adding colcemid (0.1 μg/ml) to the culture approximately 30 minutes before harvesting the cells.

The cells were collected by centrifugation and resuspended in a hypotonic buffer (60 mM KCl) at room temperature for about 30 minutes. The sample was washed three times with the fixative mixture methanol:acetic acid 3:1 at room temperature. After the last wash the sample was fixed in the fixative at −20° C. for 20 minutes. Chromosome spreads were prepared by spotting a suitable amount of the suspension onto a clean and cool slide and air-drying the slide.

Denaturing and hybridization

A binding partner of formula (VIIq) comprising polymerized moieties of formula (VII) was synthesized as described above. The binding partner (VIIq) comprised 17 nucleobases complementary to a sequence from the centromer region HSSATX (obtained from the database Genebank) of the X chromosome. The sequence of the binding partner was as follows:

Bio-L-L-AAC-TGA-ACG-GAA-AGC-AA-$NH_2$ (VIIq)

wherein Bio denotes a biotin label, and each L designates a —NH($CH_2CH_2O)_2$—$CH_2$(O)—. The concentration of the binding partner was 100 nM.

The air-dried chromosome spreads (prepared as described above) were each covered with 15 μl hybridization solution.

The hybridization solution contained 0.3×SSC (45 mM NaCl, 4.5 mM sodium citrate pH 7.0), 60% formamide v/v (Life Technologies, U.S.A., 55150B), 0.1% Triton X-100® and the respective binding partner. The specimen was covered with a coverslip in order to avoid evaporation and drying out during incubation. The slides were placed on a hot-plate (Pactronic, Buch & Holm A/S, Denmark) equilibrated at 60° C. and incubated for 5 minutes (denaturing and hybridization are performed simultaneously).

Removal of any unbound and any non-specifically bound binding partner

Following denaturing and hybridization, the coverslips were removed, and the slides were transferred to a jar with washing buffer of 0.1×SSC (15 mM NaCl, 1.5 mM sodium citrate pH 7.0) and 0.1% Triton X-100®, and washed for 5 minutes at 50° C. in a waterbath with gentle shaking.

Detection of hybrids formed

Following the post hybridization wash, the hybrids formed were detected by incubation with fluorescein labelled streptavidin (DAKO F0422 diluted 1:50 in TBS buffer pH 7.6) for 10 minutes in a humid chamber at room temperature. After incubation, excess conjugate was tapped off and the slides were briefly washed in deionized water for 1 minute at room temperature.

The slides were mounted using Vectashield Mounting Medium (Vector H-1000) containing 0.5 μg/ml Propidium iodide (Sigma). The slides were inspected by fluorescent microscopy (Leica DM RB).

Conclusions

Two strong green/yellow fluorescent spots were observed on each chromosome spread in the specimen corresponding to the two X chromosomes (chromosomes are easily recognized by red fluorescence) indicating strong specific binding. No non-specific binding was observed.

EXAMPLE 18

In situ hybridization for the detection of X chromosome specific sequences in chromosome metaphase spreads Preparation of samples Metaphase chromosome spreads were prepared as described in Example 17.

Denaturing and hybridization

A binding partner of formula (VIIr) comprising polymerized moieties of formula (VII) were synthesized as described above. The binding partner (VIIr) comprised 17 nucleobases complementary to a sequence from the centromer region HSSATX (obtained from the database Genebank) of the X chromosome. The sequence of the binding partner was as follows:

Flu-βAla-Lys-(Flu-βAla)-AAC-TGA-ACG-GAA-AGC-AA-$NH_2$ (VIIr)

wherein each Flu denotes a 5-(and 6)-carboxyfluorescein or fluorescein isothiocyanate label. The binding partner of formula (VIIr) terminates in a branched labelled end ("zipper") wherein the label is composed of a peptide label (Ala and Lys) and a fluorescein label, namely Flu-βAla-Lys-(Flu-βAla)-.

The concentration of the binding partner was 100 nM.

The air-dried chromosome spreads (prepared as described above) were each covered with 15 μl hybridization solution. The hybridization solution consisted of 10 mM NaCl (Merck, Germany, 6404.5000), 10% dextran sulphate w/v (Sigma U.S.A., D-8906), 60% formamide v/v (Life Technologies, U.S.A., 55150B), 0.1% sodium pyrophosphate, 0.2% polyvinylpyrrolidone (MW 40000), 0.2% ficoll (MW 400000), 5 mM $Na_2$EDTA, 0.05M Tris/HCl, pH 7.5 and the binding partner indicated above.

The specimen was covered with a coverslip in order to avoid evaporation and drying out during incubation. The slides were placed on a hot-plate (Pactronic, Buch & Holm A/S, Denmark) equilibrated at 60° C. and were incubated for 5 minutes (denaturing and hybridization were thus performed simultaneously).

Removal of any unbound and any non-specifically bound binding partner

Following the denaturing and hybridization the coverslips were removed and the slides were transferred to a jar with washing buffer 0.1×SSC (15 mM NaCl, 1.5 mM sodium citrate pH 7.0) and 0.1% Triton X-100® and washed for 5 minutes at 50° C. in a waterbath with gentle shaking.

Detection of hybrids formed

Following the post hybridization wash, the slides were washed for 2 minutes in TBS buffer pH 7.6 at room temperature followed by a brief wash in deionized water for 1 minute at room temperature.

The slides were mounted using Vectashield Mounting Medium (Vector H-1000) containing 0.5 μg/ml Propidium Iodide (Sigma). The slides were inspected by fluorescent microscopy (Leica DM RB).

Conclusions

Two strong green/yellow fluorescent spots were observed on each chromosome spread in the specimen corresponding to the two X chromosomes (chromosomes are easily recognized by red fluorescence) indicating strong specific binding. No non-specific binding was observed.

We claim:

1. A method for detecting the presence of specific RNA sequences in a sample of eukaryotic origin using in situ hybridization which method comprises the steps of
   (1) producing a preparation of said sample, during which step the sample is subject to fixation,
   (2) contacting said preparation with a hybridization solution comprising at least one binding partner capable of hybridizing to a specific RNA sequence to be detected so as to form hybrids and a hybrid destabilizing agent in an amount effective to decrease the melting temperature of hybrids formed between said RNA and said binding partner so as to increase the ratio between specific binding and non-specific binding, said binding partner being a polymeric strand containing polymerized moieties having a non-cyclic backbone, the polymeric strand being capable of hybridizing to the RNA sequence to be detected;
   (3) removing any unbound and any non-specifically bound binding partner;
   (4) detecting the presence of bound binding partner in the preparation thereby detecting the presence of specific RNA sequences.

2. A method for detecting the presence of specific RNA sequences in a sample of eukaryotic origin using in situ hybridization which method comprises the steps of
   (1) producing a preparation of said sample, during which step the sample is subject to fixation,
   (2) contacting said preparation with a hybridization solution comprising at least one binding partner capable of hybridizing to a specific RNA sequence to be detected so as to form hybrids and a hybrid destabilizing agent in an amount greater than 10% and effective to decrease the melting temperature of hybrids formed between said RNA and said binding partner so as to increase the ratio between specific binding and non-specific binding, said binding partner being a polymeric strand containing polymerized moieties having a non-cyclic backbone, the polymeric strand being capable of hybridizing to the RNA sequence to be detected,
   (3) removing any unbound and any non-specifically bound binding partner, and
   (4) detecting the presence of bound binding partner in the preparation thereby detecting the presence of specific RNA sequences.

3. A method according to claim 1 or 2, wherein the polymeric strand comprises polymerized moieties of formula (I)

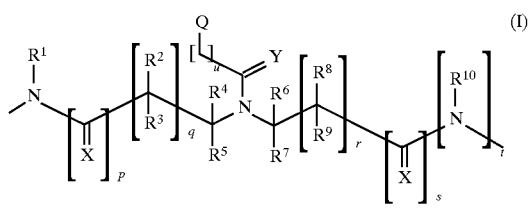

wherein Y designates O or S, each X independently designates O or S, each Q designates a ligand that independently is a naturally occurring nucleobase, a non-naturally occurring nucleobase, an intercalator, a nucleobase-binding group, a label or H, u is an integer from 1 to 5, p and s independently designate 0 or 1, q and r independently designate 0 or 1, t designates 0 or 1, $R^1$ and $R^{10}$ independently designate H or $C_{1-4}$ alkyl, $R^2, R^3, R^4, R^5, R^6, R^7, R^8$ and $R^9$ independently designate H, the side chain of a naturally occurring amino acid or the side chain of a non-naturally occurring amino acid.

4. A method according to claim 3, wherein u, p, q, r, s, Y, X and Q are as defined in claim 2, t is 0, $R^1$ designates H or $CH_3$, $R^3$, $R^4$, $R^6$ and $R^9$ designate H, and $R^2$, $R^5$, $R^7$ and $R^8$ independently designate H or the side chain of a naturally occurring amino acid or the side chain of a non-naturally occurring amino acid.

5. A method according to claim 3, wherein the polymeric strand comprises polymerized moieties of formula (II), which are moieties of the general formula (I) wherein r is 0 and q and s are 1,

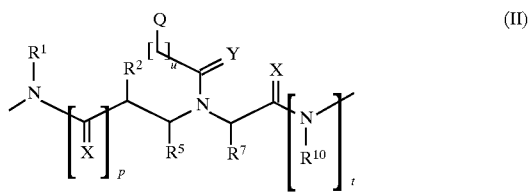

wherein Y, X, Q, p, t and u are as defined in claim 2, $R^2$, $R^5$ and $R^7$ independently designate H, the side chain of a naturally occurring amino acid or the side chain of a non-naturally occurring amino acid, and $R^1$ and $R^{10}$ independently designate H or $CH_3$.

6. A method according to claim 3, wherein the polymeric strand comprises polymerized moieties of formula (III), which are moieties of the general formula (I) wherein p, r and t are 0 and q and s are 1

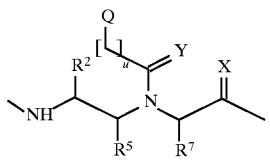

(III)

wherein Y, X, Q and u are as defined in claim 2, $R^2$, $R^5$ and $R^7$ independently designate H, the side chain of a naturally occurring amino acid or the side chain of a non-naturally occurring amino acid.

7. A method according to claim 3, wherein the polymeric strand comprises polymerized moieties of formulas (IV)–(VI), which are moieties of the general formula (I) wherein p, r and t are 0 and u, s and q are 1,

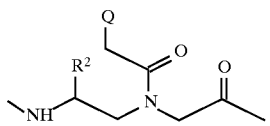

(IV)

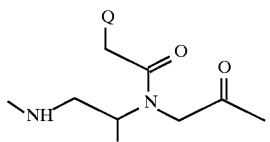

(V)

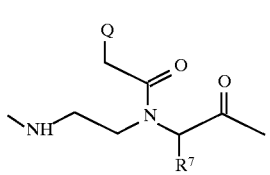

(VI)

wherein $R^2$, $R^5$ and $R^7$ designate H, the side chain of a naturally occurring amino acid or the side chain of a non-naturally occurring amino acid, and each Q independently designates a naturally occurring nucleobase, a non-naturally occurring nucleobase, an intercalator or a nucleobase-binding group.

8. A method according to claim 7, wherein $R^2$, $R^5$ and $R^7$ designate H or the side chain of Ala, Asp, Cys, Glu, His, HomoCys, Lys, Orn, Ser or Thr, and Q designates thymine, adenine, cytosine, guanine, uracil or hypoxanthine.

9. A method according to claim 3, wherein the polymeric strand comprises polymerized moieties of formula (VII), which are moieties of formula (I) wherein p, r and t are 0 and u, s and q are 1,

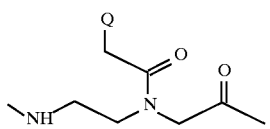

(VII)

wherein Q designates thymine, adenine, cytosine, guanine, uracil or hypoxanthine.

10. A method according to claim 3, wherein the polymeric strand is made up of from 8 to 30 polymerized moieties of the formula (I)–(VII).

11. A method according to claim 1, wherein polymerized moieties of formulas (IV)–(VII) constitute at least 75% by weight of the polymeric strand.

12. A method according to claim 1, wherein the concentration of the hybrid destabilizing agent is above 10%.

13. A method according to claim 12 or 2, wherein the hybrid destabilizing agent is selected from the group consisting of formamide, ethylene glycol and glycerol.

14. A method according to claim 13, wherein the hybrid destabilizing agent is formamide in a concentration from 30% to 50%.

15. A method according to claim 13, wherein the hybrid destabilizing agent is ethylene glycol in a concentration from 50% to 65%.

16. A method according to claim 1 or 2, wherein the sample of eucaryotic origin is a tissue section, a cell smear, or a suspension of cells or parts thereof.

17. A method according to claim 1, wherein the binding partner further comprises one or more labels which may be identical or different.

18. A method according to claim 17, wherein the label is selected from the group consisting of fluorescent labels, biotin, digoxigenin, dinitro benzoic acid, peptide labels, rhodamine, R-phycoerythrine and cyanine dyes.

19. A method according to claim 18, wherein at least one label is a fluorescent label.

20. A method according to claim 19, wherein the unbound and non-specifically bound binding partner in step (3) is removed using a washing buffer at alkaline pH.

21. A method according to claim 20, wherein the washing buffer in step (3) has a pH value of from 8 to 10.5.

22. The method according to claim 1, wherein said RNA is mRNA, rRNA or nuclear RNA.

23. A method for determining the presence of specific RNA sequences in a sample of a eucaryotic origin using in situ hybridization which method comprises the steps of (1) producing a preparation of said sample, whereby the sample will be subject to fixation, (2) contacting said preparation with a hybridization solution comprising at least one binding partner capable of hybridizing to a specific RNA sequence to be detected so as to form hybrids and a hybrid destabilizing agent in an amount effective to decrease the melting temperature of hybrids formed between said RNA and said binding partner so as to increase the ratio between specific binding and non-specific binding, said binding partner being a polymeric strand containing from 8 to 30 polymerized moieties having a non-cyclic backbone, the polymeric strand being capable of hybridizing to the RNA sequence to be determined, (3) removing any unbound and any non-specifically bound binding partner, and (4) determining the presence of bound binding partner in the preparation thereby detecting the presence of specific RNA sequences.

* * * * *